United States Patent
Bando et al.

(10) Patent No.: US 9,447,402 B2
(45) Date of Patent: Sep. 20, 2016

(54) METHOD FOR PRODUCING RECOMBINANT PROTHROMBIN, VECTOR DNA, AND REAGENT KIT

(71) Applicant: SYSMEX CORPORATION, Kobe-shi (JP)

(72) Inventors: Takahiko Bando, Sanda (JP); Mutsumi Sugai, Fujimino (JP)

(73) Assignee: SYSMEX CORPORATION, Hyogo (JP)

( * ) Notice: Subject to any disclaimer, the term of this patent is extended or adjusted under 35 U.S.C. 154(b) by 122 days.

(21) Appl. No.: 14/202,046

(22) Filed: Mar. 10, 2014

(65) Prior Publication Data

US 2014/0273040 A1   Sep. 18, 2014

(30) Foreign Application Priority Data

Mar. 15, 2013 (JP) ................. 2013-053566

(51) Int. Cl.
| | | |
|---|---|---|
| *C12Q 1/56* | (2006.01) | |
| *C12N 5/07* | (2010.01) | |
| *C12N 5/10* | (2006.01) | |
| *C12N 9/74* | (2006.01) | |
| *C12N 9/64* | (2006.01) | |

(52) U.S. Cl.
CPC ............. *C12N 9/6429* (2013.01); *C12N 9/647* (2013.01); *C12Q 1/56* (2013.01); *C07K 2319/20* (2013.01); *C07K 2319/24* (2013.01); *C07K 2319/35* (2013.01); *C12N 2710/14143* (2013.01)

(58) Field of Classification Search
CPC .............................. C12N 9/6429; C12N 9/647
USPC ..................................... 435/13, 348
See application file for complete search history.

(56) References Cited

U.S. PATENT DOCUMENTS

2004/0197858 A1   10/2004   Yonemura et al.
2009/0137001 A1    5/2009   Onchi et al.

FOREIGN PATENT DOCUMENTS

| JP | 2002-306163 A | 10/2002 |
| WO | 2005/003313 A2 | 1/2005 |
| WO | 2007/120809 A1 | 10/2007 |

OTHER PUBLICATIONS

So (1992, Korean Biochem. J. 25:60-65).*
Kost (2005, Nature Biotechnology, 23:567-575).*
Liu (2008, Protein Expression and Purification, 62:21-28).*
Davis et al., "New Fusion Protein Systems Designed to Give Soluble Expression in *Escherichia coli*", Biotechnology and Bioengineering, John Wiley & Sons, Inc., Nov. 20, 1999, vol. 65, No. 4, 7 total pages.
Susumu Maeda, "Gene Transfer Vectors of a Baculovirus, Bombyx Mori Nuclear Polyhedrosis Virus, and Their Use for Expression of Foreign Genes in Insect Cells", Invertebrate Cell System Applications, 1989, pp. 167-181, vol. 1.
Kenji Soejima, et al., "An Efficient Refolding Method for the Preparation of Recombinant Human Prethrombin-2 and Characterization of the Recombinant-Derived α-Thrombin", J. Biochem, 2001, pp. 269-277, vol. 130, No. 2.

* cited by examiner

*Primary Examiner* — Valarie Bertoglio
(74) *Attorney, Agent, or Firm* — Sughrue Mion, PLLC

(57) ABSTRACT

The present invention provides a method for producing recombinant prothrombin. The method comprises: providing a vector DNA into which a gene encoding a tag and a gene encoding prothrombin are incorporated, wherein the tag is selected from the group consisting of MBP, SUMO, and NusA; and expressing a tag fusion type prothrombin in a lepidopteran insect or cultured cells of the lepidopteran insect.

8 Claims, 11 Drawing Sheets

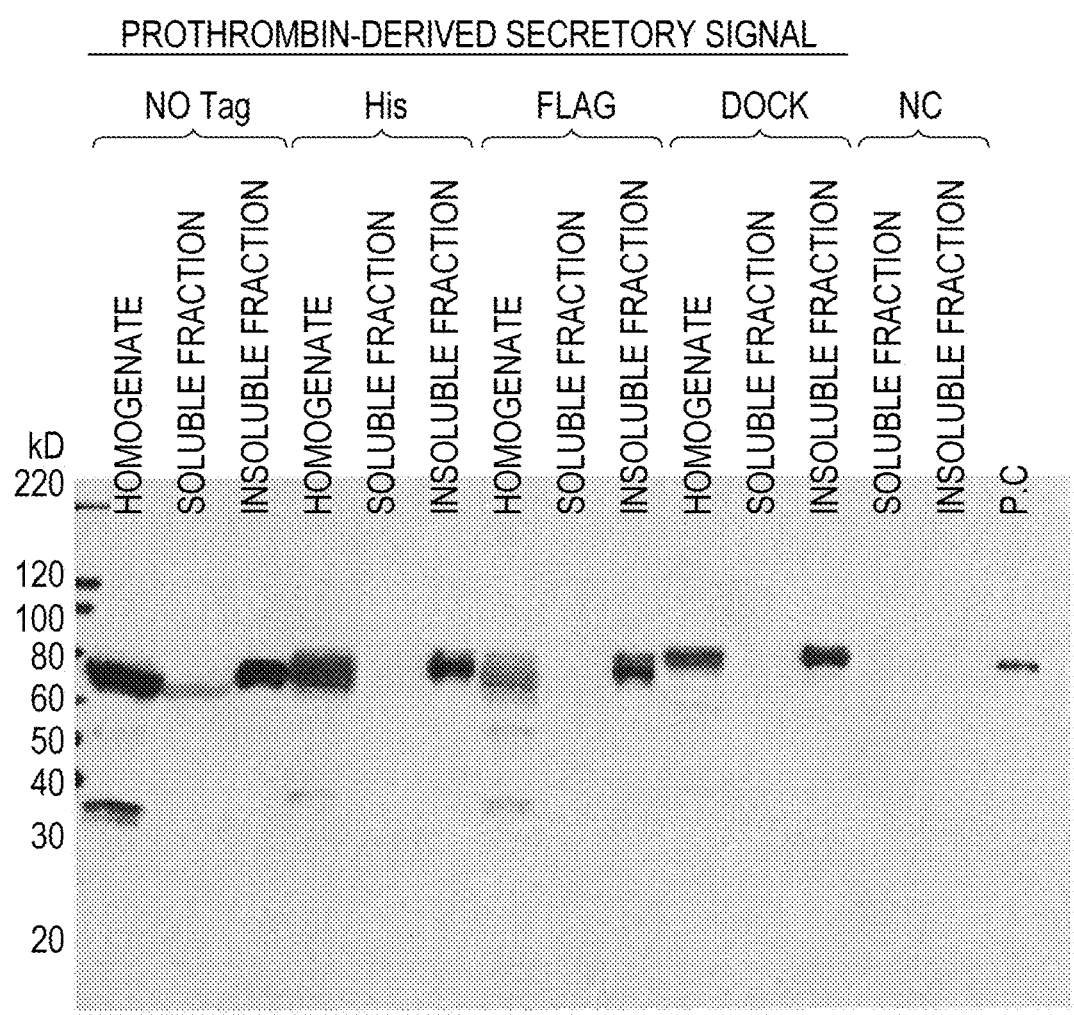

METHOD FOR PRODUCING RECOMBINANT PROTHROMBIN, VECTOR DNA, AND REAGENT KIT

FIELD OF THE INVENTION

The present invention relates to a method for producing recombinant prothrombin, vector DNA, and a reagent kit.

BACKGROUND

Prothrombin is a thrombin precursor protein having a molecular weight of about 72,000 which is produced in the liver and is also called "blood coagulation factor II". Limited proteolysis of prothrombin in vivo with the complex of activated factor X, activated factor V, phospholipids, and calcium ions results in conversion into thrombin. Thrombin is a serine protease that converts fibrinogen to fibrin by limited proteolysis in the blood-clotting reaction as well as an important protein involved in hemostasis, wound healing or the like. Therefore, the thrombin is used not only as a hemostatic agent or blood test reagent in the clinical field, but also as a reagent for study in the molecular biology field, etc.

Since a large amount of thrombin is present in the plasma, thrombin as a preparation or reagent is mainly prepared by using the plasma from human or bovine as a raw material. However, there is a risk such that infectious materials such as hepatitis virus, human immunodeficiency virus, and abnormal prion are mixed in those raw materials. Further, the plasma is a naturally-occurring raw material and thus a difference between the production lots causes a problem. Therefore, the methods for producing thrombin from the prothrombin or prethrombin produced by the recombinant DNA technique using *Escherichia coli* or mammalian cells have been recently studied and developed (Japanese Patent Application Laid-Open (JP-A) No. 2002-306163, US 2004/197858, and US 2009/137001).

SUMMARY OF THE INVENTION

The scope of the present invention is defined solely by the appended claims, and is not affected to any degree by the statements within this summary.

It is known that almost all of the expression of prothrombin or prethrombin in *Escherichia coli* results in an insoluble aggregate called an inclusion body. Therefore, it is necessary to perform refolding after solubilization of the recovered insoluble aggregate with a denaturant. However, it is known that the refolding is complicated and the refolding efficiencies of proteins having complicated structures such as prothrombin or prethrombin are very low. Further, in the thrombin obtained from the thrombin precursor solubilized by refolding, the specific activity (an activity per unit weight) is low. This leads to concerns. For example, the article of Soejima K. et al. (J. Biochem. vol. 130, p. 269-277, 2001) teaches that thrombin is prepared from prethrombin-2 obtained in the *Escherichia coli* expression system. Further, it shows that the percentage of the thrombin having an enzyme activity among the proteins solubilized by refolding is from about 4 to 7%. That is, the specific activity of the thrombin obtained from the thrombin precursor solubilized by refolding is from about 4 to 7% of that of a native form thrombin derived from plasma.

It is possible to produce a soluble prothrombin or prethrombin in the expression system using mammalian cells. However, there are problems that the yield is very low and the manufacturing cost is also high from the viewpoint of industrial-scale production.

On the other hand, a recombinant protein with a functional tag protein fused to a desired protein may be expressed in the expression system using *Escherichia coli* or mammalian cells. Examples of tags for purifying recombinant proteins include 6×His, glutathione-S-transferase (GST), FLAG, and maltose binding protein (MBP) tags. In recent years, tag proteins which improve the expression level and solubility of recombinant proteins have been developed. For example, an MBP tag and a small ubiquitin-like modifier (SUMO) tag are known as tags which improve the protein solubility. The solubility of recombinant proteins has been improved in the expression system using *Escherichia coli* or yeast (US 2009/305342 and US 2007/037246).

However, it is known that even if the solubility as the whole protein having a solubilization tag fused is maintained, a target protein portion does not have a regular structure, and thus the protein may not have an original activity. Thus, in the recombinant protein soluble in appearance due to fusion of the solubilization tag, if the solubilization tag is cleaved, the protein may become an insoluble aggregate or lose its activity.

In view of the above circumstances, the present inventors have aimed at providing a method for producing recombinant prothrombin which satisfies both the condition where a soluble prothrombin can be produced simply and in a large amount, and the condition where thrombin converted from the obtained prothrombin has a high specific activity.

The present inventors have conducted intensive examinations. As a result, they have found that a soluble prothrombin can be obtained simply and in a large amount by expressing prothrombin with a predetermined tag fused in the expression system using a lepidopteran insect and thrombin converted from the obtained prothrombin has a high specific activity. Thus, they have completed the present invention.

That is, the present invention provides a method for producing recombinant prothrombin. The method comprises: providing a vector DNA into which a gene encoding a tag and a gene encoding prothrombin are incorporated, wherein the tag is selected from the group consisting of MBP, SUMO, and NusA; and expressing a tag fusion type prothrombin in a lepidopteran insect or cultured cells of the lepidopteran insect.

Further, the present invention provides a vector DNA into which a gene encoding a tag and a gene encoding prothrombin are incorporated, wherein the tag is selected from the group consisting of MBP, SUMO, and NusA.

The present invention provides a reagent kit comprising: a thrombin reagent comprising a thrombin; and a diluent buffer for diluting plasma of a subject. The thrombin in the thrombin reagent is obtained from a tag fusion type prothrombin which is expressed in a lepidopteran insect or cultured cells of the lepidopteran insect using a vector DNA into which a gene encoding a tag and a gene encoding prothrombin are incorporated, wherein the tag is selected from the group consisting of MBP, SUMO, and NusA.

According to the present invention, soluble recombinant prothrombin can be produced simply and in a large amount. Therefore, according to the present invention, the refolding of an insoluble aggregate is not needed. Further, the resulting recombinant prothrombin is activated so that recombinant thrombin with a specific activity nearly equal to that of the native form thrombin can be obtained.

BRIEF DESCRIPTION OF THE DRAWINGS

FIG. 4A shows a photograph showing the expression levels of prothrombin in samples prepared from pupae of *Bombyx mori* in which each tag fusion type prothrombin or the prothrombin without a tag are expressed;

DETAILED DESCRIPTION OF THE PREFERRED EMBODIMENTS

Figures 1A, 1B, 1C, 1D:
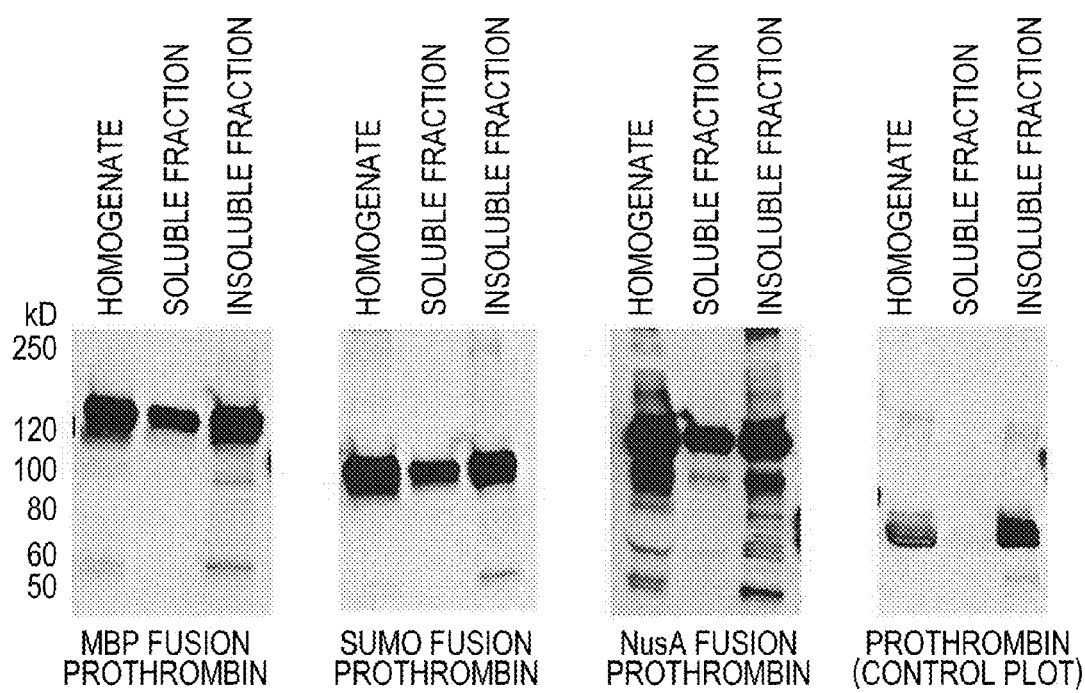
FIGS. 1A to 1D show photographs showing the expression levels of prothrombin in samples prepared from pupae of *Bombyx mori* in which each tag fusion type prothrombin of the present invention or the prothrombin without a tag are expressed.

The preferred embodiments of the present invention will be described hereinafter with reference to the drawings.

In the method for producing prothrombin of the present invention (hereinafter, simply referred to as "production method"), a vector DNA into which a gene encoding a tag selected from the group consisting of MBP, SUMO, and NusA and a gene encoding prothrombin are incorporated is used.

MBP is a protein having a molecular weight of about 42 kDa and is known to be involved in the transport of maltodextrin in Gram-negative bacteria. In the embodiment of the present invention, a gene encoding MBP is not particularly limited as long as it is an isolated gene which encodes an MBP protein well-known as a recombinant protein tag or its derivative. It is preferably a gene encoding *E. coli*-derived MBP, more preferably a gene encoding an amino acid sequence represented by SEQ ID NO: 1.

SUMO is a kind of ubiquitin-like proteins called sentrin, SMT3, PIC1, GMP1 or UBL1 and is known to be highly preserved in from yeasts to vertebrates including humans. In the embodiment of the present invention, a gene encoding SUMO is not particularly limited as long as it is an isolated gene which encodes the SUMO protein well-known as a recombinant protein tag or its derivative. It is preferably a gene encoding yeast SUMO (SMT3), human SUMO-3 or SUMOstar (modified SUMO, LifeSensors Inc.), more preferably a gene encoding an amino acid sequence represented by SEQ ID NO: 2.

NusA is a protein having a molecular weight of about 55 kDa and is known as a transcription elongation factor bound to RNA polymerase. In the embodiment of the present invention, a gene encoding NusA is not particularly limited as long as it is an isolated gene which encodes the NusA protein well-known as a recombinant protein tag or its derivative. It is preferably a gene encoding *E. coli*-derived NusA or Nus-Tag (trademark, Merck), more preferably a gene encoding an amino acid sequence represented by SEQ ID NO: 3.

The gene encoding prothrombin is not particularly limited as long as it is an isolated prothrombin gene derived from desired animal species with prothrombin (or blood coagulation factor II). Preferably, it is a gene encoding human prothrombin. In this regard, the base sequence of human prothrombin gene itself is well-known. For example, it is registered as the accession number NM_000506 in the database of the National Center for Biotechnology Information (NCBI) of the U.S. National Library of Medicine.

The vector DNA is not particularly limited as long as the DNA has a promoter capable of expressing a gene in a lepidopteran insect or cultured cells of the insect and can insert the gene into the downstream of the promoter. Preferably, it is a transfer vector capable of producing a recombinant baculovirus having the gene inserted by homologous recombination with baculovirus DNA. The vector DNA itself is well-known in the art. Examples thereof include pM02, pYNG, pBM030, pBM050, and pVL1392. In this regard, the promoter can be appropriately selected from promoters well-known in the art. Examples thereof include polyhedrin promoter, p10 promoter, and *Bombyx mori* actin promoter.

In the vector DNA into which the above genes are incorporated, a gene encoding tag fusion type prothrombin is incorporated into the downstream of the promoter. Here, the gene encoding a tag may be inserted into either the upstream or downstream of the gene encoding prothrombin. Preferably, it is inserted into the upstream of the gene encoding prothrombin. That is, the gene encoding a tag is preferably incorporated into the vector DNA so that the tag is fused to the N terminal of prothrombin. Specifically, a gene encoding an amino acid sequence represented by any one of SEQ ID NOS: 7 to 9 is preferably incorporated into the vector DNA. Here, when prothrombin is converted to thrombin, the N terminal of prothrombin is cleaved. Accordingly, when a tag is fused to the N terminal of prothrombin, the removal of the tag can be performed simultaneously by the operation of converting prothrombin to thrombin.

In the embodiment of the present invention, a gene encoding a protein secretory signal sequence is preferably further incorporated into the vector DNA. The protein secretory signal sequence may be appropriately selected from well-known sequences used in the production of recombinant prothrombin or the expression system utilizing a lepidopteran insect. Examples thereof include a prothrombin-derived secretory signal sequence (SEQ ID NO: 4), a *Bombyx mori*-derived 30K signal sequence (SEQ ID NO: 5), and a *Bombyx mori*-derived SP signal sequence (SEQ ID NO: 6).

In the embodiment of the present invention, the *Bombyx mori*-derived 30K signal sequence and a gene encoding human prothrombin with a tag fused to its N terminal are preferably incorporated into the vector DNA.

In the production method of the present invention, the tag fusion type prothrombin is expressed in a lepidopteran insect or cultured cells of the insect by using the vector DNA. Here, the lepidopteran insect is not particularly limited as long as it is a well-known lepidopteran insect suitable for expressing recombinant proteins. Examples thereof include *Bombyx mori, Spilosoma imparilis, Antheraea pernyi, Spodoptera frugiperda*, and *Trichoplusiani*. Among them, *Bombyx mori* is particularly preferred. Further, the cultured cells of the lepidopteran insect are not particularly limited as long as they are cell lines established from lepidopteran insects suitable for expressing recombinant proteins. Examples thereof include BmN, BmN4, SpIm, Anpe, Sf9, Sf21, and High5.

In the embodiment of the present invention, the tag fusion type prothrombin is preferably expressed in a lepidopteran insect from the viewpoint of producing a large amount of the recombinant prothrombin. In this regard, the lepidopteran insect may be at any stage of imago, pupa, and larva. From the viewpoint of the activity of serine protease, and the sensitivity to baculovirus, it is preferable to use a pupa of the lepidopteran insect.

The means for expressing a tag fusion type prothrombin in a lepidopteran insect or cultured cells of the lepidopteran insect is not particularly limited and it may be appropriately determined according to the kind of the vector DNA. For example, a lepidopteran insect or cultured cells of the insect may be directly transfected with a vector DNA by a well-known transgenic method in order to express the tag fusion type prothrombin. In a preferred embodiment of the present invention, a lepidopteran insect or cultured cells of the insect is infected with a baculovirus recombined with the vector DNA in order to express the tag fusion type prothrombin.

The method for recombining a baculovirus with a DNA having a desired base sequence itself is well-known in the art. For example, when the vector DNA is a transfer vector, a recombinant baculovirus may be obtained by co-transfection of the baculovirus DNA after linearization with a restriction enzyme and the vector DNA having a gene encoding a tag fusion type prothrombin incorporated into cultured cells of a lepidopteran insect, and screening of the infected cells.

In the embodiment of the present invention, the kind of baculovirus is not particularly limited as long as it is a virus with which the lepidopteran insect or cultured cells of the insect can be infected. A nuclear polyhedrosis virus (NPV) or its recombinant virus is preferred. Examples of viruses include recombinant baculoviruses infective to hosts (*Bombyx mori* of the family Bombycidae and *Autographa californica* of the family Noctuidae) such as BmNPV, HycuNPV, AnpeNPV, and AcNPV, (refer to JP-A No. 2003-52371). In a preferred embodiment, a cysteine protease defective (CPd) baculovirus is used (refer to Japanese Patent Application No. 7-303488).

The means for infecting a lepidopteran insect or cultured cells of the insect with a recombinant baculovirus is not particularly limited and it may be appropriately selected from well-known methods in the art. For example, in order to infect the lepidopteran insect, a method of injecting a solution containing a recombinant baculovirus into the insect is used. In order to infect the cultured cells, the solution containing a recombinant baculovirus may be added to a culture medium. The tag fusion type prothrombin can be expressed by infecting a lepidopteran insect or cultured cells of the insect with a virus and breeding the insect or culturing the cells for five to eight days.

In the embodiment of the present invention, the means for obtaining a tag fusion type prothrombin from a lepidopteran insect or cultured cells of the insect in which the tag fusion type prothrombin is expressed in the above manner is not particularly limited. For example, in the case of a lepidopteran insect, the tag fusion type prothrombin may be obtained by collecting a body fluid or crushing the insect to prepare a homogenate. In the case of cultured cells, the tag fusion type prothrombin may be obtained by physically crushing the cells or dissolving them in a solution containing a cell dissolving agent such as a surfactant.

Here, in the production method of present invention, the solubility of the expressed recombinant prothrombin is significantly improved. Thus, a large amount of tag fusion type prothrombin is contained in the soluble fraction. Therefore, in the embodiment of the present invention, it is preferable to further include the step of obtaining a soluble fraction containing the tag fusion type prothrombin from the lepidopteran insect or cultured cells of the insect obtained in the expression step. The soluble fraction may be obtained by filtering or centrifuging the body fluid, homogenate, cell disrupted solution or cell lysate of the lepidopteran insect obtained in the above manner and separating the supernatant. In the centrifugation process, an appropriate buffer may be optionally added to a sample. The buffer is not particularly limited as long as it is a buffer suitable for storing a protein. Examples thereof include Tris buffers and phosphate buffers.

In the embodiment of the present invention, the resulting recombinant prothrombin may be converted into thrombin by any well-known method in the art. The method is not particularly limited and examples thereof include a method including reacting ecarin (i.e., a prothrombin activating enzyme) with the recombinant prothrombin to obtain thrombin. Further, the specific activity of the resulting thrombin may be measured by any well-known method in the art. For example, the specific activity may be calculated by reacting S-2238 (i.e., a chromogenic synthetic substrate for thrombin, SEKISUI MEDICAL CO., LTD.) with the recombinant thrombin for a predetermined time, adding a reaction termination solution thereto, and measuring the absorbance.

The scope of the present invention includes a baculovirus recombined with a vector DNA into which a gene encoding a tag selected from the group consisting of MBP, SUMO, and NusA and a gene encoding prothrombin are incorporated. The production and use of the baculovirus are the same as described in the production method of the present invention. In the embodiment of the present invention, it is preferable to use a baculovirus recombined with a vector DNA into which a gene encoding a protein secretory signal sequence is further incorporated.

Further, the scope of the present invention also includes a kit for producing recombinant prothrombin which includes the vector DNA into which a gene encoding a tag selected from the group consisting of MBP, SUMO, and NusA and a gene encoding prothrombin are incorporated. The production and use of the vector DNA included in the kit are the same as described in the production method of the present invention.

In the embodiment of the present invention, the vector DNA is preferably incorporated into the baculovirus. Alternatively, in another embodiment, the vector DNA and the baculovirus may be put in different containers. Preferably, a gene encoding a protein secretory signal sequence is further incorporated into the vector DNA.

Further, the scope of the present invention includes a tag fusion type prothrombin which is expressed in a lepidopteran insect or cultured cells of the lepidopteran insect using the vector DNA into which a gene encoding a tag selected from the group consisting of MBP, SUMO, and NusA and a gene encoding prothrombin are incorporated. The method for producing a tag fusion type prothrombin is the same as described in the production method of the present invention.

The scope of the present invention also includes a thrombin reagent containing a thrombin fragment obtained from the tag fusion type prothrombin.

The thrombin reagent of the present invention may also contain a well-known stabilizer to stabilize thrombin. The stabilizer is not particularly limited as long as it is a substance which is usually used for the thrombin reagent. Examples thereof include calcium ions, organic acids, surfactants, and proteins.

Calcium ions are preferably provided in such a manner that a water-soluble calcium compound is added to the reagent. Examples of calcium compounds include calcium chloride, calcium lactate, calcium gluconate, calcium glucuronate, and calcium tartrate. One kind of these calcium compounds may be used alone, or two or more kinds thereof may be used in combination. The stabilization effective amount of the calcium compound(s) to thrombin is not particularly limited as long as the amount improves the stability of the thrombin reagent. The concentration of the calcium compound(s) in the thrombin reagent is, for example, preferably from 5 to 100 mM, more preferably from 10 to 50 mM.

Examples of organic acids include formic acid, acetic acid, propionic acid, butyric acid, valeric acid, oxalic acid, malonic acid, succinic acid, gluconic acid, lactic acid, glucuronic acid, glycolic acid, tartaric acid, malic acid, citric acid, tartaric acid, glutaric acid, aminoacetic acid, and aminocaproic acid. These organic acids may be used in the form of either free acid or salt thereof. Further, one kind of the organic acids may be used alone, or two or more kinds thereof may be used in combination. The additive amount of the organic acids is not particularly limited as long as the amount improves the stability of the thrombin reagent. The surfactant concentration in the thrombin reagent is, for example, preferably from 10 to 500 mM, more preferably from 50 to 200 mM.

The surfactant may be appropriately selected from anionic surfactants, cationic surfactants, zwitterionic surfactants, and nonionic surfactants. Examples of anionic surfactants include sodium dodecyl sulfate, sodium dodecyl sulfonate, sodium dodecyl-N-sarcosinate, sodium cholate, sodium deoxycholate, and sodium taurodeoxycholate. Examples of cationic surfactants include cetyltrimethylammonium bromide, tetradecylammonium bromide, and dodecylpyridinium chloride. Examples of zwitterionic surfactants include 3-[(3-cholamidepropyl)dimethylammonio]-1-propanesulfonic acid (CHAPS), 3-[(3-cholamidepropyl)dimethylammonio]-2-hydroxy-1-propanesulfonic acid (CHAPSO), palmitoyllysolecithin, dodecyl-N-betaine, and dodecyl-β-alanine. Examples of nonionic surfactants include octyl glucoside, heptyl thioglucoside, decanoyl-N-methylglucamide, polyoxyethylene dodecyl ether, polyoxyethylene heptamethylhexyl ether, polyoxyethylene isooctylphenyl ether (Triton™ X series), polyoxyethylene nonylphenyl ether, polyoxyethylene fatty acid ester, sucrose fatty acid ester, and polyoxyethylene sorbitol ester (Tween® series).

Among these surfactants, nonionic surfactants are particularly preferred. One kind of these surfactants may be used alone, or two or more kinds thereof may be used in combination. The additive amount of the surfactants is not particularly limited as long as the amount improves the stability of the thrombin reagent. The surfactant concentration in the thrombin reagent is, for example, preferably from 0.001 to 1% by weight/volume, more preferably from 0.005 to 0.1% by weight/volume.

Examples of proteins as stabilizers include albumin, gelatin, and globulin. One kind of these proteins may be used alone, or two or more kinds thereof may be used in combination. The additive amount of the proteins is not particularly limited as long as the amount improves the stability of the thrombin reagent. The protein concentration in the thrombin reagent is, for example, preferably from 0.05 to 10% by weight/volume, more preferably from 0.1 to 5% by weight/volume.

The above stabilizers are selected taking into consideration influences of thrombin on enzyme activity during storage of thrombin in liquid, dried or frozen form, when a dried product is dissolved, or when a frozen product is melted. Further, when a plurality of stabilizers are used in combination, in the case of a liquid product of thrombin, the stabilizers are added to the liquid product. In the case of a dried or frozen product of thrombin, the stabilizers are prepared so that stabilization effects are exerted when the product finally becomes the form of liquid and then added to the dried or frozen product.

The thrombin reagent of the present invention may also contain a buffer. The buffer may be appropriately selected from buffers having a buffering capacity at a pH range of 4 to 9 and used. As the buffer, for example, one kind of buffers such as citric acid, phosphoric acid, acetic acid, imidazole, GTA, HEPES, MOPS, BIS-TRIS, TRIS, MOPSO, ADA, and MES may be used alone, or two or more kinds thereof may be used in combination. The additive amount of these buffers is not particularly limited as long as it is the amount of a buffering capacity. Regarding the additive amount of the buffers, for example, the concentration in the thrombin reagent is preferably from 5 to 1000 mM, more preferably from 50 to 500 mM.

The thrombin reagent of the present invention may also contain high molecular polysaccharides. Examples of high molecular polysaccharides include dextran 40, dextran 70, dextran 200,000, dextran 500,000, and Ficoll. One kind of those high molecular polysaccharides may be used alone, or two or more kinds thereof may be used in combination. The additive amount of these high molecular polysaccharides is not particularly limited as long as the amount improves reproducibility. The concentration of the high molecular polysaccharides in the thrombin reagent is, for example, preferably from 0.1 to 10% by weight/volume, more preferably from 0.3 to 3% by weight/volume.

The thrombin reagent of the present invention may also contain synthetic polymers. Examples of synthetic polymers include polyvinyl alcohol 500, polyvinyl alcohol 1500, polyvinyl alcohol 2000, polyethylene glycol 1500, polyethylene glycol 2000, polyethylene glycol 4000, polyethylene glycol 6000, polyethylene glycol 8000, polyethylene glycol 20000, and polyvinylpyrrolidone. One kind of these synthetic polymers may be used alone, or two or more kinds thereof may be used in combination. The additive amount of these synthetic polymers is not particularly limited as long as the amount improves reproducibility. The concentration of the synthetic polymers in the thrombin reagent is, for example, preferably from 0.1 to 10% by weight/volume, more preferably from 0.3 to 3% by weight/volume.

Further, an appropriate preservative may be added to the thrombin reagent of the present invention. As the preservative, for example, one kind of ciprofloxacin, propionic acid, and sodium benzoate may be used alone, or two or more kinds thereof may be used in combination. Further, a salt such as sodium chloride or a usual stabilizer such as an amino acid or sugar may be contained in the reagent, if necessary.

The thrombin content in the thrombin reagent of the present invention is not particularly limited as long as the activity is adjusted to a target value.

As a specific thrombin reagent, for example, a pH 6.0 solution consisting of 200 U/mL thrombin and a buffer containing acetic acid and calcium lactate may be used.

The thrombin reagent of the present invention may be a liquid product, a frozen product, or a dried product. When the thrombin reagent of the present invention is a dried product, it is dissolved by adding purified water or a buffer.

The concentration described above is the concentration in the liquid product and the concentration of the dried product or the like is the concentration when dissolved in water or the like before use.

The scope of the present invention also includes a clotting function test reagent kit which includes the thrombin reagent and a diluent buffer for diluting plasma of a subject.

Examples of diluent buffers included in the clotting function test reagent kit of the present invention include Good buffers such as MES, Bis-Tris, ADA, PIPES, ACES, MOPSO, BES, MOPS, TES, HEPES, DIPSO, TAPSO, POPSO, HEPPSO, EPPS, Tricine, Bicine, TAPS, CHES, CAPSO, and CAPS; and a barbital buffer. Further, examples thereof include a TC buffer (manufactured by SYSMEX CORPORATION).

The clotting function test reagent kit of the present invention may further include a normal solution which contains a predetermined concentration of fibrinogen. In this case, the clotting function test reagent kit of the present invention can be used as a fibrinogen quantitative reagent. A procedure for quantifying fibrinogen is specifically as follows. First, normal solutions are diluted 5-, 10-, and 20-fold with a diluent buffer (the dilution rate may be appropriately adjusted). Subsequently, each of the diluted normal solutions (0.2 mL) is heated at 37° C. for 3 minutes. 0.1 mL of a test reagent or thrombin reagent previously heated to 37° C. is added to each of the solutions. The clotting time is measured and the measured values of the diluted normal solutions are plotted on a graph to produce a calibration curve. Then, a plasma sample is diluted 10-fold with a diluent buffer (the dilution rate may be appropriately adjusted). The clotting time of the resulting diluted sample is measured in the same manner as described above. On the basis of the resulting clotting time, the concentration may be calculated from the calibration curve.

The clotting function test reagent kit of the present invention may be used to measure activities of thrombin inhibitors, such as activities of antithrombin, hirudin, and chemosynthetic inhibitors.

The thrombin reagent and the diluent buffer are separately packaged in the clotting function test reagent kit. For example, the thrombin reagent is put in a first reagent container and the diluent buffer is put in a second reagent container. Further, when the clotting function test reagent kit further includes the normal solution which contains a predetermined concentration of fibrinogen, the normal solution is put in a third reagent container other than the first and second reagent containers. In this regard, the clotting function test reagent kit may include another reagent which is put in another reagent container, if desired. Further, the clotting function test reagent kit may include one or more kinds of buffers for diluting one or more kinds of reagents, instructions for use, a container usable for reactions and the like, if desired.

Hereinafter, the present invention will be described in detail with reference to examples, however the present invention is not limited to the examples.

EXAMPLES

Example 1

Production of Baculovirus into which Tag and Human Prothrombin Genes are Incorporated (1) Cloning of Human Prothrombin Gene On the basis of the base sequence of human prothrombin gene (NCBI Acc. No. NM_000506) published on the database (hereinafter also referred to as "hPTH gene"), a primer set for cloning hPTH gene was designed. The sequences of each primer are as follows:

```
                                         (SEQ ID NO: 10)
F:    5'-AAGAATTCATGGCCAACACCTTCTTGGAGGAG-3';
and
                                         (SEQ ID NO: 11)
R:    5'-AATCTAGACTACTCTCCAAACTGATCAATGACCTT-3'.
```

The hPTH gene was isolated using the primer sets by the PCR method using a human liver cDNA library (Clontech Laboratories, Inc.) as a template. The isolated DNA fragment was purified using QIAquick (QIAGEN) and treated with restriction enzymes EcoRI and XbaI. The resulting fragment was incorporated into a multi-cloning site of pM02 vector (SYSMEX CORPORATION). The resulting plasmid construct is referred to as "pM02-hPTH".

(2) Subcloning of Gene Encoding Tag

On the basis of base sequences of the reported malE, SUMO, and NusA genes, primer sets for subcloning the genes were designed. The sequences of the primers are shown as follows:

```
malE gene primer set
                                         (SEQ ID NO: 12)
F:   5'-AAGGTACCATGAAAATAAAAACAGGTGCGC-3'
                                         (SEQ ID NO: 13)
R:   5'-TTGAATTCGCTCTGAAAGTACAGATCCTCAGTCTGCGC-3'

SUMO gene primer set
                                         (SEQ ID NO: 14)
F:   5'-AAGGTACCATGTCCCTGCAGGACTCAG-3'
                                         (SEQ ID NO: 15)
R:   5'-TTGAATTCGCTCTGAAAGTACAGATCCTCAATCTGTTCTC-3'
```

-continued

```
NusA gene primer set
                                          (SEQ ID NO: 16)
F:   5'-AAGAATTCGCTCTGAAAGTACAGATCCTCCGCTTCGTCAC-3'
                                          (SEQ ID NO: 17)
R:   5'-AAGGTACCATGAACAAAGAAATTTTGGCTGTAG-3'.
```

The malE gene was isolated using the malE gene primer set by the PCR method using pMAL-p5x (New England Biolabs) as a template. Similarly, the SUMO and NusA genes were respectively isolated using the SUMO gene primer set and the NusA gene primer set by the PCR method using pI SUMOstar (LifeSensors Inc.) and pET-44 (+) (Merck) as templates.

(3) Production of Vector DNA into which Gene Encoding Tag and Prothrombin Gene are Incorporated The isolated DNA fragments of tag genes were purified using QIAquick (QIAGEN) and treated with restriction enzymes EcoRI and KpnI. Then, the resulting DNA fragments of the genes were incorporated into the upstream of the hPTH gene in pM02-hPTH to prepare the vector DNAs (transfer plasmids) of the present invention. The resulting transfer plasmids are referred to as "pM02-MBP-hPTH, pM02-SUMO-hPTH, and pM02-NusA hPTH", respectively.

(4) Production of Recombinant Baculovirus

Recombinant baculovirus was produced by modifying the method of Maeda et al. (Invertebrate Cell system and Applications, Vol. 1, p. 167-181, CRC Press, Boca Raton (1989)). The specific procedure is as follows. First, the transfer plasmids were purified using Plasmid purification kit (QIAGEN). Then, these transfer plasmids (0.5 µg) and DNA (0.2 µg) of CPd baculovirus (ATCC VR2500) after linearization were co-transfected into BmN cells (Maeda, 1989) using a lipofection reagent (X-tremeGENE 9 DNA-Transfection Reagent: Roche). Screening was performed by the limiting dilution method using a 96-well plate. The virus presented with the symptoms of infection was selected and the culture supernatant was recovered. As a result, the recombinant baculovirus of the present invention into which a gene encoding a tag and a prothrombin gene were incorporated was obtained. In the case of pM02-hPTH, the recombinant baculovirus was produced in the same manner as described above.

(5) Examination of Expression of Tag Fusion Type Prothrombin in BmN Cells

The supernatant was recovered to prepare a lysate of BmN cells. The obtained lysate was analyzed by SDS-PAGE and Western blotting. In the Western blotting, a mouse antithrombin antibody (NOVUS) was used as a primary antibody, anti-mouse IgG (Dako) was used as a secondary antibody, and Immobilon Western HRP reagent (Millipore) was used as a detection reagent. As a result, it was confirmed that a protein having a molecular weight assumed to be the tag fusion type prothrombin was expressed in the BmN lysate.

Example 2

Examination of Expression and Specific Activity of Tag Fusion Type Prothrombin in *Bombyx mori*

(1) Expression of Tag Fusion Type Prothrombin

The recombinant baculovirus produced in Example 1 was inoculated into pupae of *Bombyx mori* (variety: Kinsyu-showa, silkworm seeds were purchased from Ueda-sanshu and developed to pupae in the laboratory of SYSMEX CORPORATION). The infected pupae were recovered seven days after the virus inoculation and frozen at −80° C. The frozen pupae were crushed with a blender. The residues of pupae in the resulting disrupted solution were removed by low-speed centrifugation and filtration to give a homogenate. The resulting homogenate was separated into a supernatant and a precipitate by centrifugation at 20000×g for 30 minutes. The resulting supernatant was defined as a soluble fraction and the precipitate was defined as an insoluble fraction.

Figure 2:
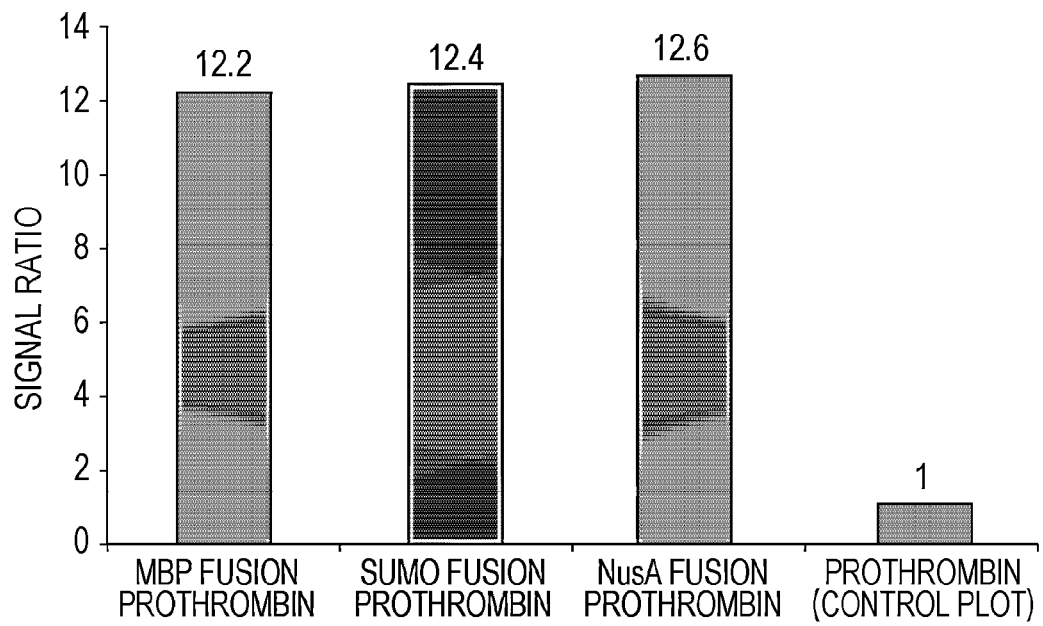
FIG. 2 is a graph showing the relative ratios of the amounts of each tag fusion type prothrombin of the present invention contained in soluble fractions.

The resulting homogenate and soluble and insoluble fractions were analyzed by SDS-PAGE and Western blotting. In the Western blotting, a mouse antithrombin antibody (NOVUS) was used as a primary antibody, anti-mouse IgG (Dako) was used as a secondary antibody, and Immobilon Western HRP reagent (Millipore) was used as a detection reagent. The results are shown in FIGS. 1A to D. On the basis of the results of Western blotting, ratios of the expression levels in the soluble fractions of each soluble tag fusion type prothrombin are shown in FIG. 2. In the graph of FIG. 2, the band intensity of a soluble fraction of the prothrombin without fusion tag (FIG. 1D: control plot) is defined as 1 and the relative ratios of the band intensities of the soluble fractions of each soluble tag fusion type prothrombin (FIGS. 1A to C) are shown.

The bands in the homogenates of FIGS. 1A to D show that both the tag fusion type prothrombin and the prothrombin without fusion tag were expressed in the pupae of *Bombyx mori*. However, the prothrombin without fusion tag was little contained in each soluble fraction. That is, it was found that, in the case of the prothrombin without fusion tag, most of the prothrombin expressed in the pupae of *Bombyx mori* was an insoluble protein. On the other hand, it was found that in each prothrombin to which MBP, SUMO or NusA was fused as a tag, a large amount of prothrombin was contained in each soluble fraction. FIG. 2 shows that the solubility of each tag fusion type prothrombin was more than or equal to about 12 times that of the prothrombin without fusion tag.

(2) Specific Activity of Tag Fusion Type Prothrombin

The soluble fractions prepared in the above process were simply purified using Q-Sepharose FastFlow (GE healthcare). Ecarin (i.e., a prothrombin activating enzyme, Sigma) was added to each of the purified soluble fractions so as to have a final concentration of 1 U/ml, followed by reaction at 37° C. for 2 hours. The resulting reaction solution was analyzed by SDS-PAGE and Western blotting using a mouse antithrombin antibody (NOVUS). In the Western blotting, a mouse antithrombin antibody (NOVUS) was used as a primary antibody, anti-mouse IgG (Dako) was used as a secondary antibody, and Immobilon Western HRP reagent (Millipore) was used as a detection reagent.

Figure 3:
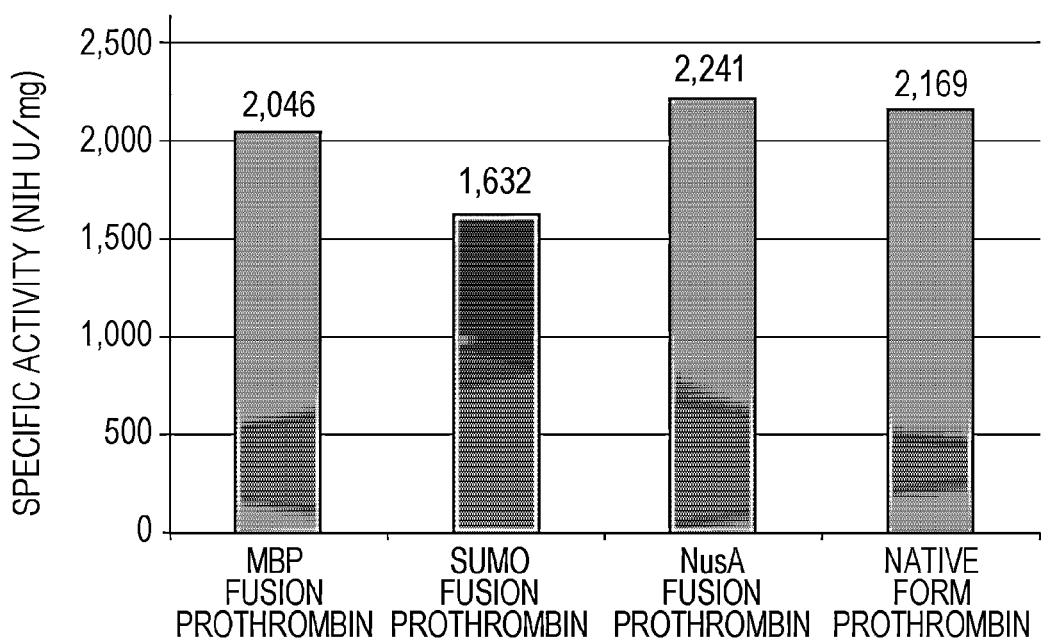
FIG. 3 is a graph showing specific activities of thrombin obtained from each tag fusion type prothrombin and a native form prothrombin.

As a result of Western blotting, it was found that each tag fusion type human prothrombin was activated by the effect of ecarin and had a molecular weight equal to that of the native form human prothrombin. The thrombin specific activity (NIH U/mg) of each tag fusion type human prothrombin was measured using a specific synthetic substrate of thrombin (S-2238, SEKISUI MEDICAL CO., LTD.). As the control, the thrombin prepared by the reaction of ecarin with the native form human prothrombin (derived from human plasma, Calbiochem) was used. The measurement results are shown in FIG. 3. According to FIG. 3, it is shown that the thrombin fragments obtained from each of the tag fusion type human prothrombin species had a specific activity equal to that of the native form thrombin.

Comparative Example 1

Figure 4B:
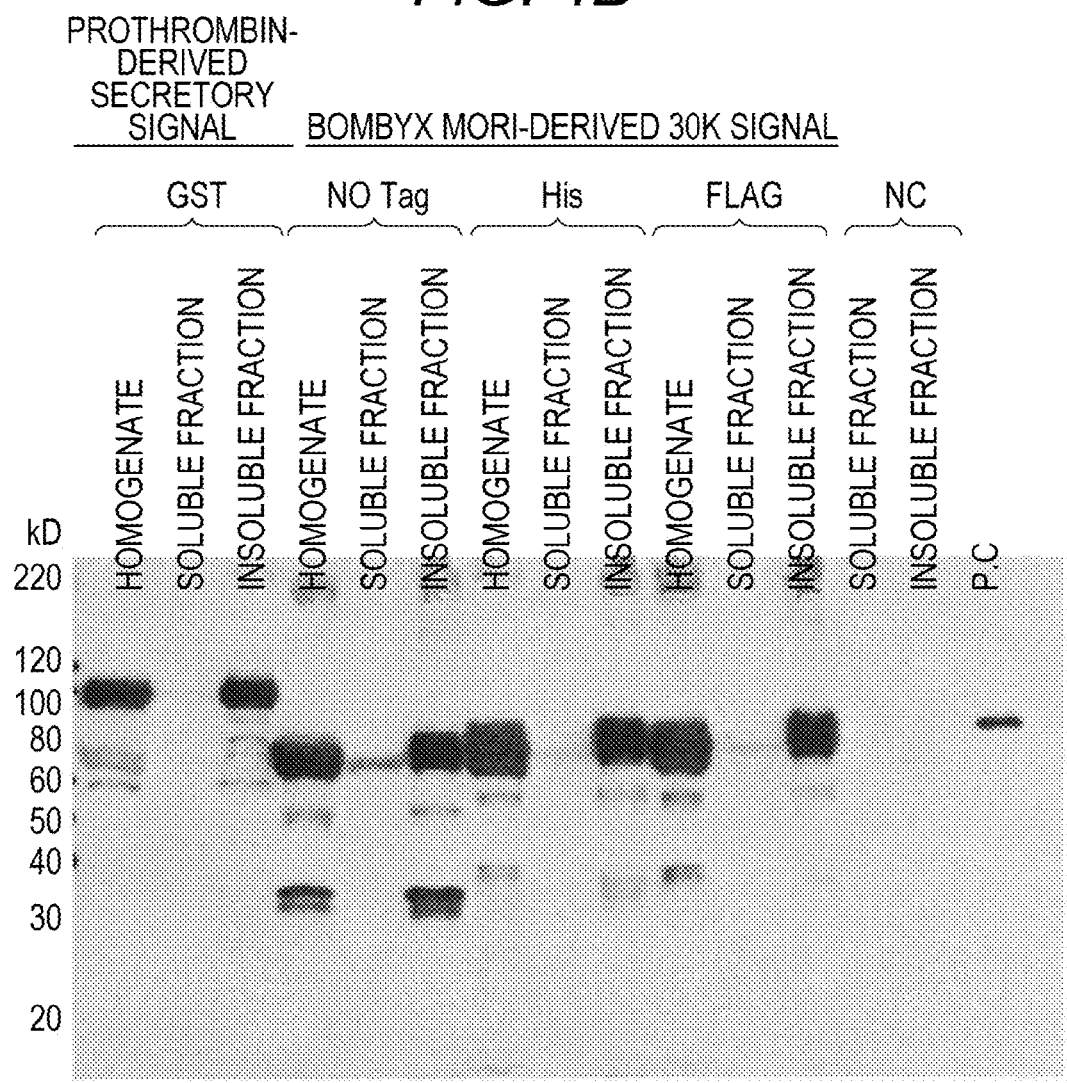
FIG. 4B shows a photograph showing the expression levels of prothrombin in samples prepared from pupae of *Bombyx mori* in which each tag fusion type prothrombin or the prothrombin without a tag are expressed.
Figure 4C:
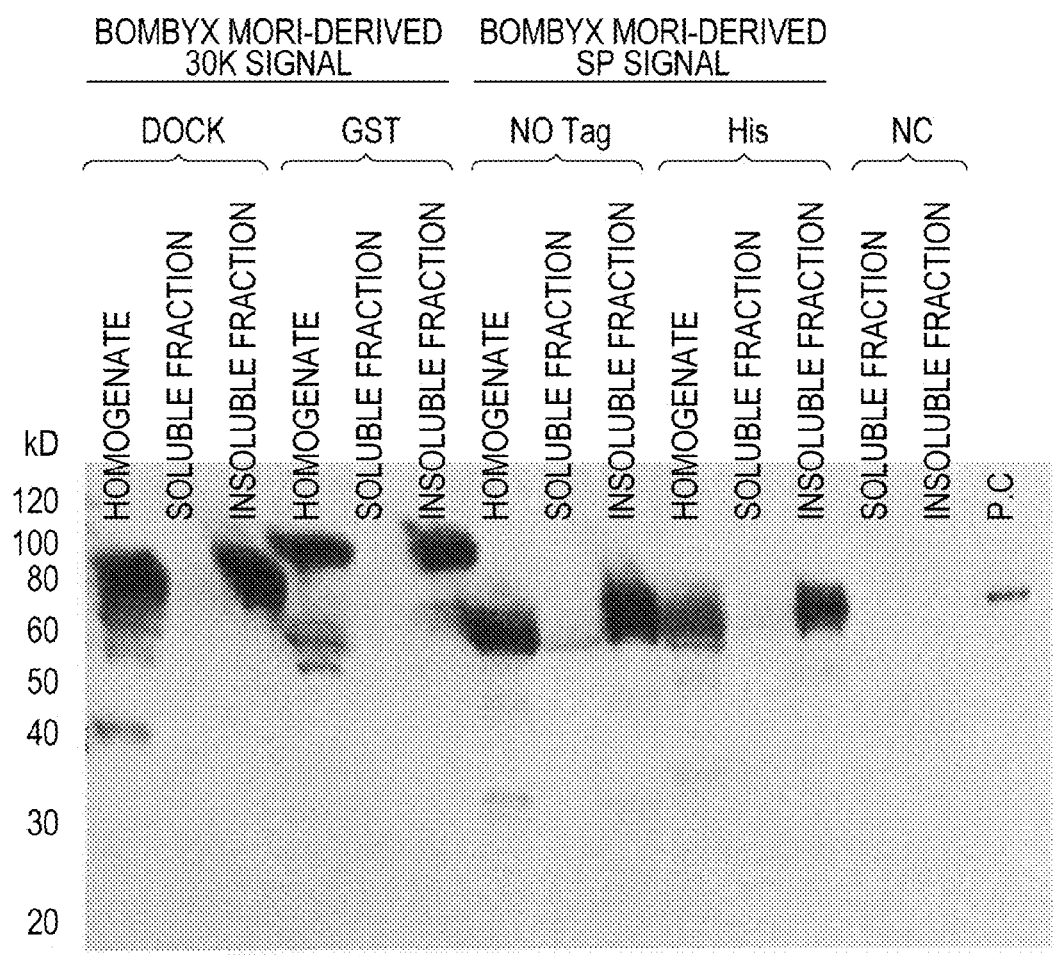
FIG. 4C shows a photograph showing the expression levels of prothrombin in samples prepared from pupae of *Bombyx mori* in which each tag fusion type prothrombin or the prothrombin without a tag are expressed.
Figure 4D:
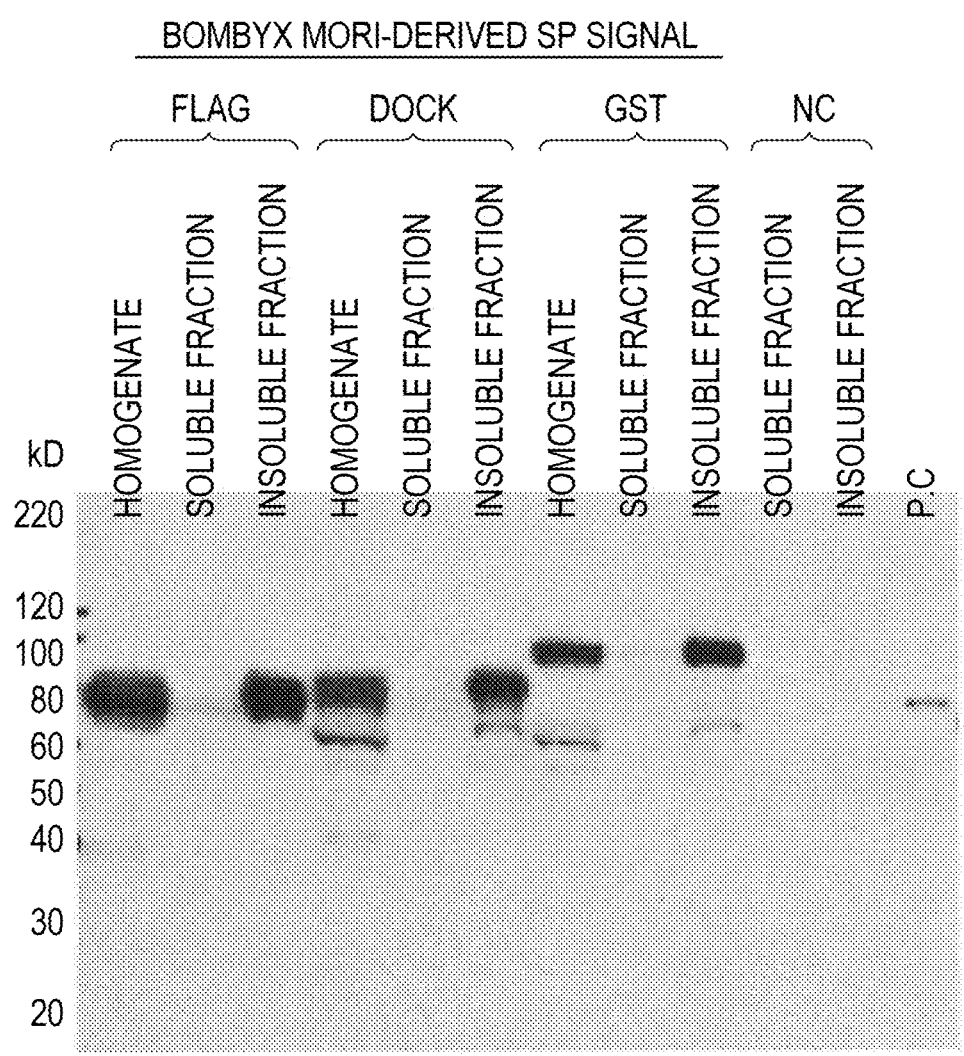
FIG. 4D shows a photograph showing the expression levels of prothrombin in samples prepared from pupae of *Bombyx mori* in which each tag fusion type prothrombin is expressed.
Figure 5:
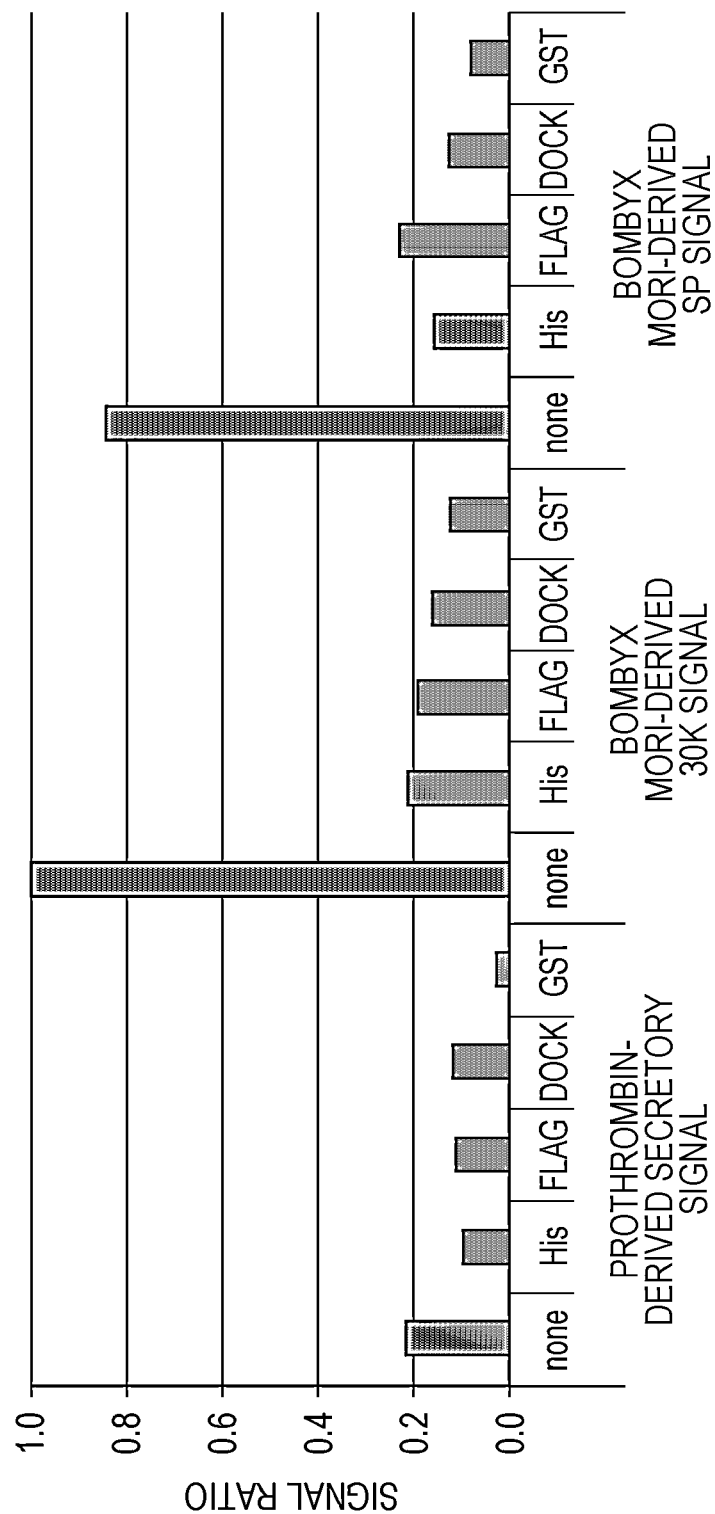
FIG. 5 is a graph showing the relative ratios of the amounts of each tag fusion type prothrombin contained in soluble fractions.
Figure 6:
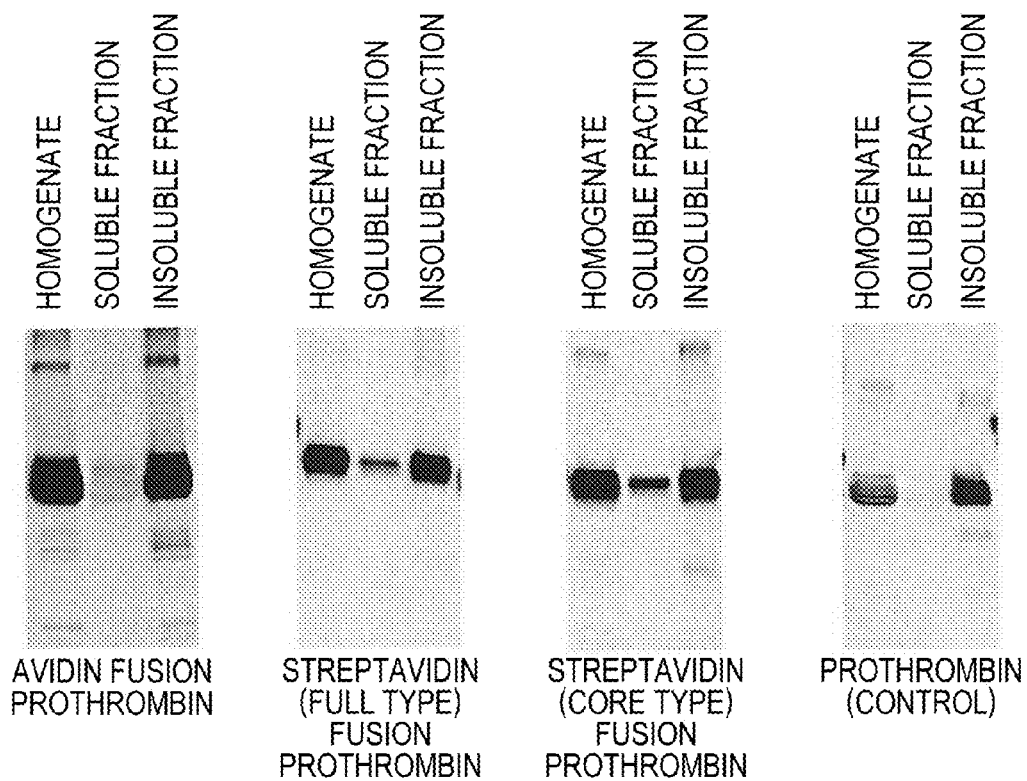
FIGS. 6A to 6D show photographs showing the expression levels of prothrombin in samples prepared from pupae of *Bombyx mori* in which each tag fusion type prothrombin or the prothrombin without a tag are expressed.

Examination of Effects of Tags Other than Tag of Present Invention and Signal Peptide In the case of expressing prothrombin by a recombinant protein expression system in *Bombyx mori*, it was examined whether tags (His, FLAG, DOCK, and GST) frequently used for an *Escherichia coli* expression system were effective in improving the solubility. Further, influences on the solubility due to the kind of signal peptide were also examined.
(1) Production of Vector DNA The hPTH gene isolated in Example 1 was incorporated into the pM01 vector (SYSMEX CORPORATION) to prepare a vector DNA with a human prothrombin-derived secretory signal at the upstream of the hPTH gene. Similarly, the hPTH gene was incorporated into the pM15 vector (SYSMEX CORPORATION), the pM23 vector (SYSMEX CORPORATION), the pM31a vector (SYSMEX CORPORATION), and the pM47 vector (SYSMEX CORPORATION), respectively, to prepare vector DNAs, having a human prothrombin-derived secretory signal, into which genes encoding human prothrombin having the 6×His, FLAG, DOCK, and GST fused to the C terminal were introduced. Then, the isolated hPTH gene was incorporated into the pM16 vector (SYSMEX CORPORATION), the pM27 vector (SYSMEX CORPORATION), the pM35a vector (SYSMEX CORPORATION), and the pM51 vector (SYSMEX CORPORATION), respectively, to prepare vector DNAs into which genes encoding human prothrombin having a *Bombyx mori*-derived 30K signal and the 6×His tag, FLAG, DOCK, and GST fused to the C terminal were introduced. Then, the isolated hPTH gene was incorporated into the pMSP-01 vector (SYSMEX CORPORATION), the pM-SP06 vector (SYSMEX CORPORATION), the pM-SP 24 vector (SYSMEX CORPORATION), the pM-SP 32 vector (SYSMEX CORPORATION), and the pM-SP 48 vector (SYSMEX CORPORATION), respectively, to prepare a vector DNA with a *Bombyx mori*-derived SP signal at the upstream of the hPTH gene and vector DNAs into which genes encoding human prothrombin having the 6×His tag, FLAG, DOCK, and GST fused to the C terminal and a *Bombyx mori*-derived SP signal were introduced.
(2) Production of Recombinant Baculovirus and Expression of Tag Fusion Type Prothrombin Recombinant baculoviruses were produced in the same manner as in Example 1 using the vector DNAs produced in the above process. Then, pupae of *Bombyx mori* were infected with the resulting recombinant baculoviruses in the same manner as in Example 2 to prepare a homogenate and soluble and insoluble fractions.
(3) Examination of Solubility of Tag Fusion Type Prothrombin The obtained homogenate and soluble and insoluble fractions were analyzed by SDS-PAGE and Western blotting. In the Western blotting, a mouse antithrombin antibody (NOVUS) was used as a primary antibody, anti-mouse IgG (Dako) was used as a secondary antibody, and ECL detection kit (GE healthcare) was used as a detection reagent. The results are shown in FIGS. 4A to D. In FIG. 4, N.C indicates uninfected *Bombyx mori* and P.C indicates the native form human prothrombin (derived from human plasma, Calbiochem). On the basis of the results of Western blotting, ratios of the expression levels in the soluble fractions of various tag fusion type prothrombin fragments are shown in FIG. 5. In the graph of FIG. 5, the band intensity of a soluble fraction of the prothrombin without a tag to which the *Bombyx mori*-derived 30K signal peptide of FIG. 4B was fused (the same conditions as the control of Example 2) is defined as 1 and the relative ratios of the band intensities of other soluble fractions are shown.

The bands in the homogenates of FIGS. 4A to D show that both the tag fusion type prothrombin and the prothrombin without fusion tag were expressed in the pupae of *Bombyx mori*. Further, little difference in the expression level due to the kind of signal peptide was observed. However, in the case of the prothrombin to which any of the tags of His, FLAG, DOCK, and GST was fussed, the prothrombin was little contained in each soluble fraction. FIG. 5 shows that the solubility of the prothrombin to which any of the tags was fused was inferior to that of the prothrombin without fusion tag. That is, it was found that even if these tags were fused, the solubility of the prothrombin expressed in the pupae of *Bombyx mori* was not improved.

Comparative Example 2

Figure 7:
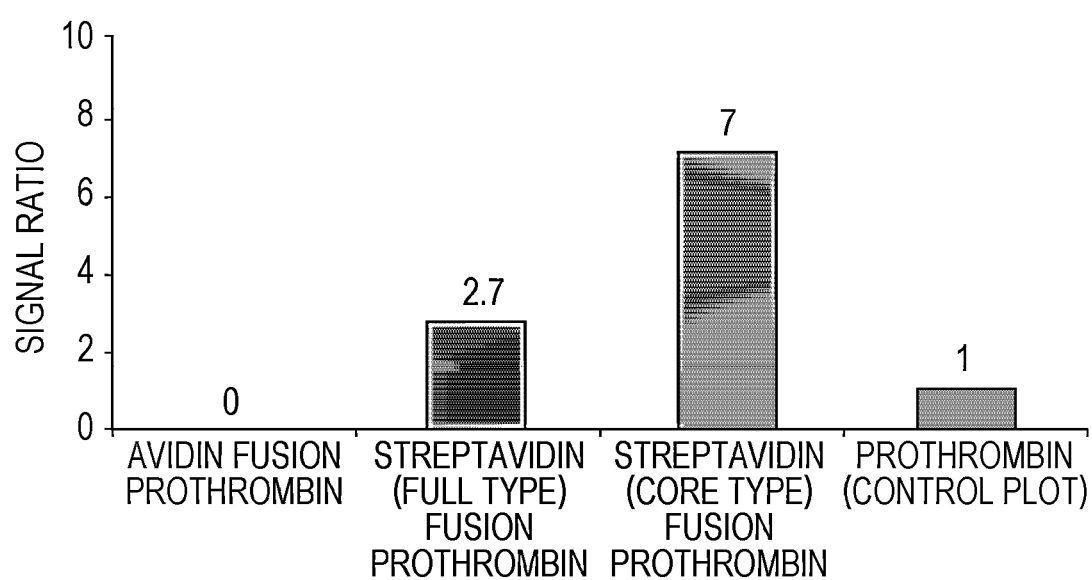
FIG. 7 is a graph showing the relative ratios of the amounts of each tag fusion type prothrombin contained in soluble fractions.

Examination of Effects of Fusion Type Proteins Other than Tag of Present Invention In the case of expressing prothrombin in a recombinant protein expression system in *Bombyx mori*, it was examined whether fusion type proteins other than the tag of the present invention (avidin, full and core types of streptavidin) were effective in improving the solubility.
(1) Production of Vector DNA On the basis of base sequences of the avidin gene (NCBI Acc. No. NM_205320.1) and the streptavidin (core or full type) gene (NCBI Acc. No. X03591.1) registered on the database, genes were prepared by artificial gene synthesis (Life Technologies). In the prepared genes, a KpnI site was added to the 5' terminal and an EcoRI site was added to the 3' terminal, followed by insertion into pUC19 (Life Technologies). These genes were purified and subjected to a restriction enzyme treatment under the same conditions as Example 1. The DNA fragments of the genes were incorporated to the upstream of the hPTH gene in pM02-hPTH to prepare vector DNAs into which genes encoding human prothrombin having the avidin gene, the streptavidin (full) gene, and the streptavidin (core) gene fused to the N terminal were introduced.
(2) Production of Recombinant Baculovirus and Expression of Tag Fusion Type Prothrombin Recombinant baculoviruses were produced in the same manner as in Example 1, using the vector DNAs produced in the above manner. Then, pupae of *Bombyx mori* were infected with the resulting recombinant baculoviruses in the same manner as in Example 2 to prepare a homogenate and soluble and insoluble fractions.
(3) Examination of Solubility of Tag Fusion Type Prothrombin The obtained homogenate and soluble and insoluble fractions were analyzed by SDS-PAGE and Western blotting. In the Western blotting, a mouse antithrombin antibody (NOVUS) was used as a primary antibody, anti-mouse IgG (Dako) was used as a secondary antibody, and Immobilon Western HRP reagent (Millipore) was used as a detection reagent. The results are shown in FIGS. 6A to D. On the basis of the results of Western blotting, ratios of the expression levels in the soluble fractions of various tag fusion type prothrombin fragments are shown in FIG. 7. In the graph of FIG. 7, the band intensity of a soluble fraction of the prothrombin without a tag (the same conditions as the control of Example 2) is defined as 1 and the relative ratios of the band intensities of other soluble fractions are shown.

The bands in the homogenates of FIGS. 6A to D show that both the tag fusion type prothrombin and the prothrombin without fusion tag were expressed in the pupae of *Bombyx mori*. It was found that almost all of the tag fusion type prothrombins were contained in the insoluble fractions. From FIG. 7, it was found that the solubility of the avidin-fused prothrombin was not improved. It was also found that the solubility of the prothrombin fused to the full or core type of streptavidin was improved as compared to the prothrombin without a tag, however, it was not sufficient.

Example 3

Preparation of Thrombin Reagent and Evaluation of Performance of Reagent (1) Preparation of Thrombin Reagent In this example, the MBP-fusion prothrombin which was used to measure the specific activity in Example 2 was used. Activation of the MBP-fusion prothrombin by ecarin resulted in formation of thrombin. The thrombin, 0.9% sodium benzoate, and a solution containing 0.2% Tween® 80 were mixed to prepare a thrombin reagent of the present invention. The thrombin activity in the present reagent was 200 U/ml.

(2) Evaluation of Performance of Thrombin Reagent

The sensitivity, accuracy, and stability of the thrombin reagent of the present invention obtained in the above manner were evaluated. The clotting time was measured using an analyzer: Coagrex-800 (manufactured by SYSMEX CORPORATION). As a sample, Control plasma N for blood coagulation test (manufactured by SYSMEX CORPORATION) was used. As a buffer, TC buffer (manufactured by SYSMEX CORPORATION) was used. As the control reagent, a commercially available reagent: Thrombocheck Fib(L) containing human-derived native form thrombin (manufactured by SYSMEX CORPORATION) was used. The thrombin activity of the control reagent was 200 U/ml.

[Evaluation of Sensitivity]

The sample was 5-, 10- or 20-fold diluted using the TC buffer. 100 µl of the resulting sample was heated at 37° C. for 1 minute. Thereafter, 50 µl of the thrombin reagent of this example or control reagent preheated was added to the sample, followed by measurement of the clotting time. The measurement was performed twice (N1 and N2).

The sensitivity was evaluated based on a difference between the average clotting time when using the 20-fold diluted sample and the average clotting time when using the 5-fold diluted sample. The results are shown in Table 1.

From Table 1, it was verified that the sensitivity of the thrombin reagent of this example was equal to that of the control reagent.

TABLE 1

| | | Reagent of this example | | | Control reagent | | |
| --- | --- | --- | --- | --- | --- | --- | --- |
| | | Dilution rate of sample | | | | | |
| | | ×5 | ×10 | ×20 | ×5 | ×10 | ×20 |
| Clotting time | N1 | 7.7 | 12.1 | 24.1 | 8.0 | 14.8 | 23.5 |
| | N2 | 7.7 | 13.5 | 23.0 | 7.9 | 15.0 | 23.1 |
| | Average | 7.7 | 12.8 | 23.6 | 8.0 | 14.9 | 23.3 |
| Clotting time difference | | | 15.9 | | | 15.4 | |

[Evaluation of Accuracy]

Figure 8A:
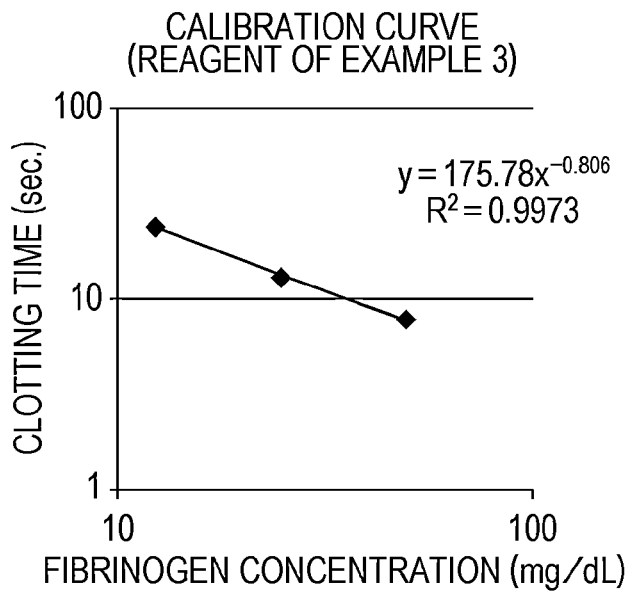
FIG. 8A is a graph showing a calibration curve created using a reagent of the present invention prepared in Example 3.
Figure 8B:
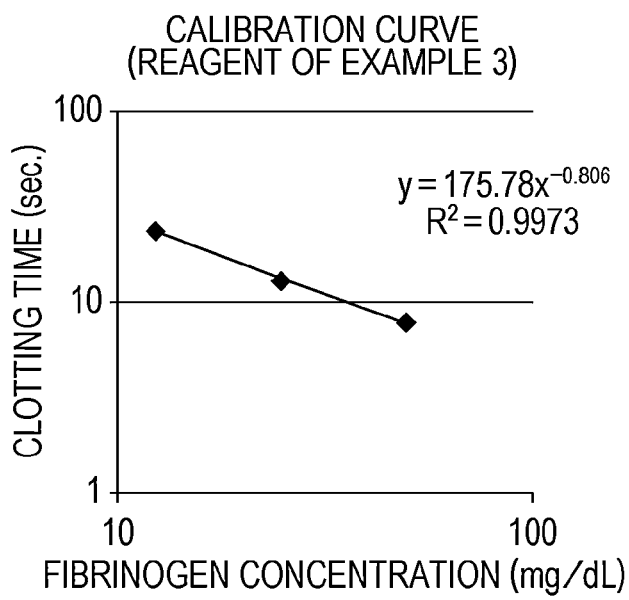
FIG. 8B is a graph showing a calibration curve created using a control reagent used in Example 3.

On the basis of the measurement result of the sensitivity test and the fibrinogen concentration of the sample, the calibration curve for quantifying the fibrinogen concentration in the sample was created (FIG. 8). The clotting time of the sample with the known fibrinogen concentration (247 mg/dL: standard) was measured by using the calibration curves. The measurement was performed twice (N1 and N2). The fibrinogen concentration was calculated by the regression equation using the measured clotting time. The results are shown in Table 2. In the case of the reagent of this example, the calculated value was 258.0 mg/dL. In the case of the control reagent, the calculated value was 224.4 mg/dL. The fibrinogen concentration was 247 mg/dL. Thus, in the case of the reagent of this example, the concentration was 104.5% based on the counter-standard. In the case of the control reagent, the concentration was 90.9% based on the counter-standard. As described above, it was verified that the accuracy of the thrombin reagent of this example was equal to that of the control reagent.

TABLE 2

| | | Reagent of this example | Control reagent |
| --- | --- | --- | --- |
| Clotting time | N1 | 12.1 | 14.8 |
| | N2 | 13.5 | 15.0 |
| | Average | 12.8 | 14.9 |
| Calculated value | | 258.0 | 224.4 |
| Counter-standard | | 104.5% | 90.9% |

[Evaluation of Stability]

Figure 9A:
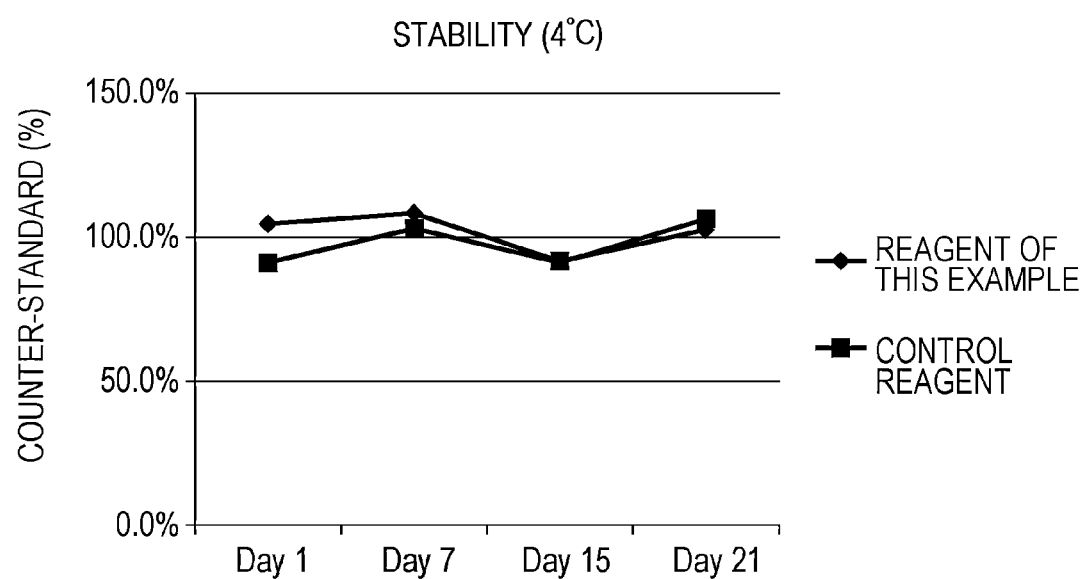
FIG. 9A is a graph showing the storage stability of the reagent of the present invention prepared in Example 3.
Figure 9B:
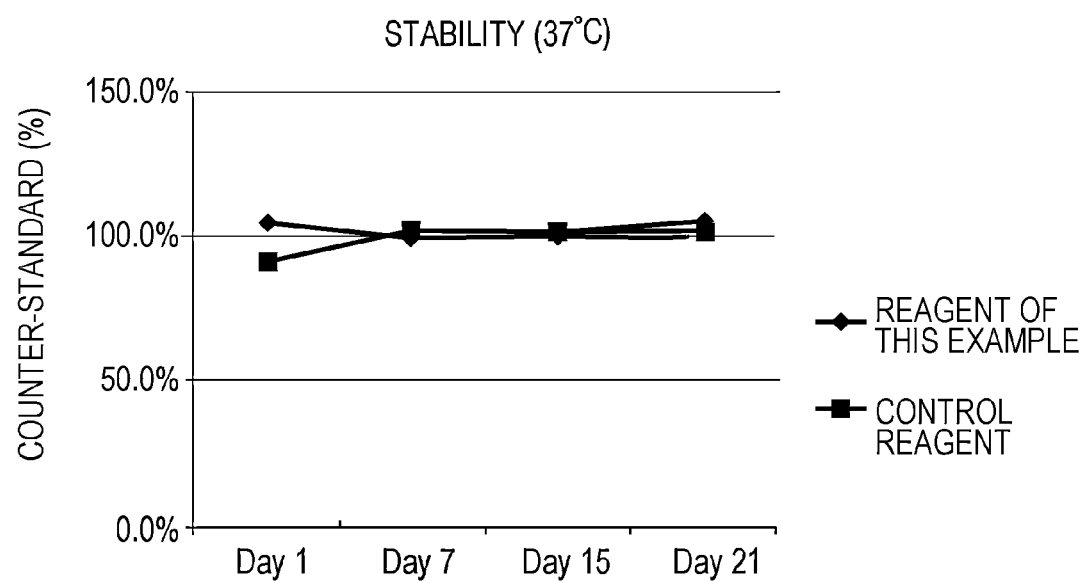
FIG. 9B is a graph showing the storage stability of the control reagent used in Example 3.

The thrombin reagent of this example and the control reagent were allowed to stand at 4° C. or 37° C. The fibrinogen concentration of the sample was measured in the same manner as the accuracy test one day, seven days, fifteen days, and twenty-one days after the standing. The results are shown in FIGS. 9A and 9B. From FIGS. 9A and 9B, it was verified that, under any temperature condition, the storage stability of the thrombin reagent of this example was equal to that of the control reagent.

What is claimed is:

1. A method for producing recombinant prothrombin, comprising:
   providing a vector DNA into which a gene encoding a tag and a gene encoding prothrombin are incorporated, wherein the tag is selected from the group consisting of MBP, SEQ ID NO: 2, and NusA; and
   expressing a tag fusion type prothrombin in a lepidopteran insect or cultured cells of the lepidopteran insect.

2. The method according to claim 1, further comprising:
   obtaining a soluble fraction containing the tag fusion type prothrombin from the lepidopteran insect or the cultured cells of the lepidopteran insect after the expressing step.

3. The method according to claim 1, wherein the gene encoding a tag is incorporated into the vector DNA so that the tag is fused to the N terminal of prothrombin.

4. The method according to claim 1, wherein a gene encoding a polypeptide having the amino acid sequence set forth in any one of SEQ ID NOS: 7 to 9 is incorporated into the vector DNA.

5. The method according to claim 1, wherein the lepidopteran insect is *Bombyx mori*.

6. The method according to claim 1, wherein the expressing step comprises infecting the lepidopteran insect or the cultured cells of the lepidopteran insect with a baculovirus comprising the vector DNA.

7. The method according to claim 1, wherein a gene encoding a protein secretory signal sequence is incorporated into the vector DNA.

8. The method according to claim 7, wherein the protein secretory signal sequence is at least one selected from the group consisting of a prothrombin-derived secretory signal sequence, a *Bombyx mori*-derived 30K signal sequence, and a *Bombyx mori*-derived SP signal sequence.

* * * * *

SEQUENCE LISTING

<160> NUMBER OF SEQ ID NOS: 17

<210> SEQ ID NO 1
<211> LENGTH: 399
<212> TYPE: PRT
<213> ORGANISM: Artificial Sequence
<220> FEATURE:
<223> OTHER INFORMATION: Synthetic Tag

<400> SEQUENCE: 1

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
    195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
    355                 360                 365

Val Arg Thr Ala Val Ile Asn Ala Ala Ser Gly Arg Gln Thr Val Asp
370                 375                 380

Glu Ala Leu Lys Asp Ala Gln Thr Glu Asp Leu Tyr Phe Gln Ser
385                 390                 395

<210> SEQ ID NO 2
<211> LENGTH: 104

<212> TYPE: PRT
<213> ORGANISM: Artificial Sequence
<220> FEATURE:
<223> OTHER INFORMATION: Synthetic Tag

<400> SEQUENCE: 2

Ser Leu Gln Asp Ser Glu Val Asn Gln Glu Ala Lys Pro Glu Val Lys
1               5                   10                  15

Pro Glu Val Lys Pro Glu Thr His Ile Asn Leu Lys Val Ser Asp Gly
                20                  25                  30

Ser Ser Glu Ile Phe Phe Lys Ile Lys Lys Thr Thr Pro Leu Arg Arg
            35                  40                  45

Leu Met Glu Ala Phe Ala Lys Arg Gln Gly Lys Glu Met Asp Ser Leu
50                  55                  60

Thr Phe Leu Tyr Asp Gly Ile Glu Ile Gln Ala Asp Gln Thr Pro Glu
65                  70                  75                  80

Asp Leu Asp Met Glu Asp Asn Asp Ile Ile Glu Ala His Arg Glu Gln
                85                  90                  95

Ile Glu Asp Leu Tyr Phe Gln Ser
            100

<210> SEQ ID NO 3
<211> LENGTH: 502
<212> TYPE: PRT
<213> ORGANISM: Artificial Sequence
<220> FEATURE:
<223> OTHER INFORMATION: Synthetic Tag

<400> SEQUENCE: 3

Met Asn Lys Glu Ile Leu Ala Val Val Glu Ala Val Ser Asn Glu Lys
1               5                   10                  15

Ala Leu Pro Arg Glu Lys Ile Phe Glu Ala Leu Glu Ser Ala Leu Ala
                20                  25                  30

Thr Ala Thr Lys Lys Lys Tyr Glu Gln Glu Ile Asp Val Arg Val Gln
            35                  40                  45

Ile Asp Arg Lys Ser Gly Asp Phe Asp Thr Phe Arg Arg Trp Leu Val
50                  55                  60

Val Asp Glu Val Thr Gln Pro Thr Lys Glu Ile Thr Leu Glu Ala Ala
65                  70                  75                  80

Arg Tyr Glu Asp Glu Ser Leu Asn Leu Gly Asp Tyr Val Glu Asp Gln
                85                  90                  95

Ile Glu Ser Val Thr Phe Asp Arg Ile Thr Thr Gln Thr Ala Lys Gln
            100                 105                 110

Val Ile Val Gln Lys Val Arg Glu Ala Glu Arg Ala Met Val Val Asp
        115                 120                 125

Gln Phe Arg Glu His Glu Gly Glu Ile Ile Thr Gly Val Val Lys Lys
    130                 135                 140

Val Asn Arg Asp Asn Ile Ser Leu Asp Leu Gly Asn Asn Ala Glu Ala
145                 150                 155                 160

Val Ile Leu Arg Glu Asp Met Leu Pro Arg Glu Asn Phe Arg Pro Gly
                165                 170                 175

Asp Arg Val Arg Gly Val Leu Tyr Ser Val Arg Pro Glu Ala Arg Gly
            180                 185                 190

Ala Gln Leu Phe Val Thr Arg Ser Lys Pro Glu Met Leu Ile Glu Leu
        195                 200                 205

Phe Arg Ile Glu Val Pro Glu Ile Gly Glu Glu Val Ile Glu Ile Lys
    210                 215                 220

Ala Ala Ala Arg Asp Pro Gly Ser Arg Ala Lys Ile Ala Val Lys Thr
225                 230                 235                 240

Asn Asp Lys Arg Ile Asp Pro Val Gly Ala Cys Val Gly Met Arg Gly
                245                 250                 255

Ala Arg Val Gln Ala Val Ser Thr Glu Leu Gly Gly Glu Arg Ile Asp
            260                 265                 270

Ile Val Leu Trp Asp Asp Asn Pro Ala Gln Phe Val Ile Asn Ala Met
            275                 280                 285

Ala Pro Ala Asp Val Ala Ser Ile Val Val Asp Glu Asp Lys His Thr
        290                 295                 300

Met Asp Ile Ala Val Glu Ala Gly Asn Leu Ala Gln Ala Ile Gly Arg
305                 310                 315                 320

Asn Gly Gln Asn Val Arg Leu Ala Ser Gln Leu Ser Gly Trp Glu Leu
                325                 330                 335

Asn Val Met Thr Val Asp Asp Leu Gln Ala Lys His Gln Ala Glu Ala
            340                 345                 350

His Ala Ala Ile Asp Thr Phe Thr Lys Tyr Leu Asp Ile Asp Glu Asp
            355                 360                 365

Phe Ala Thr Val Leu Val Glu Glu Gly Phe Ser Thr Leu Glu Glu Leu
        370                 375                 380

Ala Tyr Val Pro Met Lys Glu Leu Leu Glu Ile Glu Gly Leu Asp Glu
385                 390                 395                 400

Pro Thr Val Glu Ala Leu Arg Glu Arg Ala Lys Asn Ala Leu Ala Thr
                405                 410                 415

Ile Ala Gln Ala Gln Glu Glu Ser Leu Gly Asp Asn Lys Pro Ala Asp
            420                 425                 430

Asp Leu Leu Asn Leu Glu Gly Val Asp Arg Asp Leu Ala Phe Lys Leu
        435                 440                 445

Ala Ala Arg Gly Val Cys Thr Leu Glu Asp Leu Ala Glu Gln Gly Ile
        450                 455                 460

Asp Asp Leu Ala Asp Ile Glu Gly Leu Thr Asp Glu Lys Ala Gly Ala
465                 470                 475                 480

Leu Ile Met Ala Ala Arg Asn Ile Cys Trp Phe Gly Asp Glu Ala Glu
                485                 490                 495

Asp Leu Tyr Phe Gln Ser
            500

<210> SEQ ID NO 4
<211> LENGTH: 24
<212> TYPE: PRT
<213> ORGANISM: Artificial Sequence
<220> FEATURE:
<223> OTHER INFORMATION: Synthetic Signal peptide

<400> SEQUENCE: 4

Met Ala His Tyr Arg Gly Leu Gln Leu Pro Gly Cys Leu Ala Leu Ala
1               5                   10                  15

Ala Leu Cys Ser Leu Tyr His Ser
            20

<210> SEQ ID NO 5
<211> LENGTH: 19
<212> TYPE: PRT
<213> ORGANISM: Artificial Sequence
<220> FEATURE:
<223> OTHER INFORMATION: Synthetic Signal peptide

```
<400> SEQUENCE: 5

Met Arg Leu Thr Leu Phe Ala Phe Val Leu Ala Val Cys Ala Leu Ala
1               5                   10                  15

Ser Asn Ala

<210> SEQ ID NO 6
<211> LENGTH: 16
<212> TYPE: PRT
<213> ORGANISM: Artificial Sequence
<220> FEATURE:
<223> OTHER INFORMATION: Synthetic Signal peptide

<400> SEQUENCE: 6

Met Arg Val Leu Val Leu Leu Ala Cys Leu Ala Ala Ala Ser Asn Ala
1               5                   10                  15

<210> SEQ ID NO 7
<211> LENGTH: 981
<212> TYPE: PRT
<213> ORGANISM: Artificial Sequence
<220> FEATURE:
<223> OTHER INFORMATION: MBP-fused prothrombin

<400> SEQUENCE: 7

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
```

```
                260                 265                 270
Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
            290                 295             300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu
                325                 330                 335

Leu Val Lys Asp Pro Arg Ile Ala Ala Thr Met Glu Asn Ala Gln Lys
            340                 345             350

Gly Glu Ile Met Pro Asn Ile Pro Gln Met Ser Ala Phe Trp Tyr Ala
                355                 360             365

Val Arg Thr Ala Val Ile Asn Ala Ala Ser Gly Arg Gln Thr Val Asp
            370                 375             380

Glu Ala Leu Lys Asp Ala Gln Thr Glu Asp Leu Tyr Phe Gln Ser Glu
385                 390                 395                 400

Phe Met Ala Asn Thr Phe Leu Glu Glu Val Arg Lys Gly Asn Leu Glu
                405                 410                 415

Arg Glu Cys Val Glu Glu Thr Cys Ser Tyr Glu Glu Ala Phe Glu Ala
                420                 425             430

Leu Glu Ser Ser Thr Ala Thr Asp Val Phe Trp Ala Lys Tyr Thr Ala
            435                 440                 445

Cys Glu Thr Ala Arg Thr Pro Arg Asp Lys Leu Ala Ala Cys Leu Glu
            450                 455             460

Gly Asn Cys Ala Glu Gly Leu Gly Thr Asn Tyr Arg Gly His Val Asn
465                 470                 475                 480

Ile Thr Arg Ser Gly Ile Glu Cys Gln Leu Trp Arg Ser Arg Tyr Pro
                485                 490                 495

His Lys Pro Glu Ile Asn Ser Thr Thr His Pro Gly Ala Asp Leu Gln
                500                 505             510

Glu Asn Phe Cys Arg Asn Pro Asp Ser Ser Thr Thr Gly Pro Trp Cys
            515                 520             525

Tyr Thr Thr Asp Pro Thr Val Arg Arg Gln Glu Cys Ser Ile Pro Val
            530                 535             540

Cys Gly Gln Asp Gln Val Thr Val Ala Met Thr Pro Arg Ser Glu Gly
545                 550                 555                 560

Ser Ser Val Asn Leu Ser Pro Pro Leu Glu Gln Cys Val Pro Asp Arg
                565                 570                 575

Gly Gln Gln Tyr Gln Gly Arg Leu Ala Val Thr Thr His Gly Leu Pro
            580                 585             590

Cys Leu Ala Trp Ala Ser Ala Gln Ala Lys Ala Leu Ser Lys His Gln
            595                 600             605

Asp Phe Asn Ser Ala Val Gln Leu Val Glu Asn Phe Cys Arg Asn Pro
610                 615                 620

Asp Gly Asp Glu Glu Gly Val Trp Cys Tyr Val Ala Gly Lys Pro Gly
625                 630                 635                 640

Asp Phe Gly Tyr Cys Asp Leu Asn Tyr Cys Glu Glu Ala Val Glu Glu
                645                 650             655

Glu Thr Gly Asp Gly Leu Asp Glu Asp Ser Asp Arg Ala Ile Glu Gly
            660                 665             670

Arg Thr Ala Thr Ser Glu Tyr Gln Thr Phe Phe Asn Pro Arg Thr Phe
            675                 680                 685
```

-continued

```
Gly Ser Gly Glu Ala Asp Cys Gly Leu Arg Pro Leu Phe Glu Lys Lys
            690                 695                 700
Ser Leu Glu Asp Lys Thr Glu Arg Glu Leu Leu Glu Ser Tyr Ile Asp
705                 710                 715                 720
Gly Arg Ile Val Glu Gly Ser Asp Ala Glu Ile Gly Met Ser Pro Trp
                725                 730                 735
Gln Val Met Leu Phe Arg Lys Ser Pro Gln Glu Leu Leu Cys Gly Ala
            740                 745                 750
Ser Leu Ile Ser Asp Arg Trp Val Leu Thr Ala Ala His Cys Leu Leu
        755                 760                 765
Tyr Pro Pro Trp Asp Lys Asn Phe Thr Glu Asn Asp Leu Leu Val Arg
    770                 775                 780
Ile Gly Lys His Ser Arg Thr Arg Tyr Glu Arg Asn Ile Glu Lys Ile
785                 790                 795                 800
Ser Met Leu Glu Lys Ile Tyr Ile His Pro Arg Tyr Asn Trp Arg Glu
                805                 810                 815
Asn Leu Asp Arg Asp Ile Ala Leu Met Lys Leu Lys Lys Pro Val Ala
            820                 825                 830
Phe Ser Asp Tyr Ile His Pro Val Cys Leu Pro Asp Arg Glu Thr Ala
        835                 840                 845
Ala Ser Leu Leu Gln Ala Gly Tyr Lys Gly Arg Val Thr Gly Trp Gly
    850                 855                 860
Asn Leu Lys Glu Thr Trp Thr Ala Asn Val Gly Lys Gly Gln Pro Ser
865                 870                 875                 880
Val Leu Gln Val Val Asn Leu Pro Ile Val Glu Arg Pro Val Cys Lys
                885                 890                 895
Asp Ser Thr Arg Ile Arg Ile Thr Asp Asn Met Phe Cys Ala Gly Tyr
            900                 905                 910
Lys Pro Asp Glu Gly Lys Arg Gly Asp Ala Cys Glu Gly Asp Ser Gly
        915                 920                 925
Gly Pro Phe Val Met Lys Ser Pro Phe Asn Asn Arg Trp Tyr Gln Met
    930                 935                 940
Gly Ile Val Ser Trp Gly Glu Gly Cys Asp Arg Asp Gly Lys Tyr Gly
945                 950                 955                 960
Phe Tyr Thr His Val Phe Arg Leu Lys Lys Trp Ile Gln Lys Val Ile
                965                 970                 975
Asp Gln Phe Gly Glu
            980

<210> SEQ ID NO 8
<211> LENGTH: 686
<212> TYPE: PRT
<213> ORGANISM: Artificial Sequence
<220> FEATURE:
<223> OTHER INFORMATION: SUMO-fused prothrombin

<400> SEQUENCE: 8

Ser Leu Gln Asp Ser Glu Val Asn Gln Glu Ala Lys Pro Glu Val Lys
1               5                   10                  15
Pro Glu Val Lys Pro Glu Thr His Ile Asn Leu Lys Val Ser Asp Gly
                20                  25                  30
Ser Ser Glu Ile Phe Phe Lys Ile Lys Lys Thr Thr Pro Leu Arg Arg
            35                  40                  45
Leu Met Glu Ala Phe Ala Lys Arg Gln Gly Lys Glu Met Asp Ser Leu
    50                  55                  60
```

```
Thr Phe Leu Tyr Asp Gly Ile Glu Ile Gln Ala Asp Gln Thr Pro Glu
65                  70                  75                  80

Asp Leu Asp Met Glu Asp Asn Asp Ile Ile Glu Ala His Arg Glu Gln
            85                  90                  95

Ile Glu Asp Leu Tyr Phe Gln Ser Glu Phe Met Ala Asn Thr Phe Leu
        100                 105                 110

Glu Glu Val Arg Lys Gly Asn Leu Glu Arg Glu Cys Val Glu Glu Thr
            115                 120                 125

Cys Ser Tyr Glu Glu Ala Phe Glu Ala Leu Glu Ser Ser Thr Ala Thr
        130                 135                 140

Asp Val Phe Trp Ala Lys Tyr Thr Ala Cys Glu Thr Ala Arg Thr Pro
145                 150                 155                 160

Arg Asp Lys Leu Ala Ala Cys Leu Glu Gly Asn Cys Ala Glu Gly Leu
                165                 170                 175

Gly Thr Asn Tyr Arg Gly His Val Asn Ile Thr Arg Ser Gly Ile Glu
            180                 185                 190

Cys Gln Leu Trp Arg Ser Arg Tyr Pro His Lys Pro Glu Ile Asn Ser
        195                 200                 205

Thr Thr His Pro Gly Ala Asp Leu Gln Glu Asn Phe Cys Arg Asn Pro
210                 215                 220

Asp Ser Ser Thr Thr Gly Pro Trp Cys Tyr Thr Thr Asp Pro Thr Val
225                 230                 235                 240

Arg Arg Gln Glu Cys Ser Ile Pro Val Cys Gly Gln Asp Gln Val Thr
                245                 250                 255

Val Ala Met Thr Pro Arg Ser Glu Gly Ser Ser Val Asn Leu Ser Pro
            260                 265                 270

Pro Leu Glu Gln Cys Val Pro Asp Arg Gly Gln Gln Tyr Gln Gly Arg
        275                 280                 285

Leu Ala Val Thr Thr His Gly Leu Pro Cys Leu Ala Trp Ala Ser Ala
        290                 295                 300

Gln Ala Lys Ala Leu Ser Lys His Gln Asp Phe Asn Ser Ala Val Gln
305                 310                 315                 320

Leu Val Glu Asn Phe Cys Arg Asn Pro Asp Gly Asp Glu Glu Gly Val
                325                 330                 335

Trp Cys Tyr Val Ala Gly Lys Pro Gly Asp Phe Gly Tyr Cys Asp Leu
            340                 345                 350

Asn Tyr Cys Glu Glu Ala Val Glu Glu Glu Thr Gly Asp Gly Leu Asp
        355                 360                 365

Glu Asp Ser Asp Arg Ala Ile Glu Gly Arg Thr Ala Thr Ser Glu Tyr
        370                 375                 380

Gln Thr Phe Phe Asn Pro Arg Thr Phe Gly Ser Gly Glu Ala Asp Cys
385                 390                 395                 400

Gly Leu Arg Pro Leu Phe Glu Lys Lys Ser Leu Glu Asp Lys Thr Glu
                405                 410                 415

Arg Glu Leu Leu Glu Ser Tyr Ile Asp Gly Arg Ile Val Glu Gly Ser
            420                 425                 430

Asp Ala Glu Ile Gly Met Ser Pro Trp Gln Val Met Leu Phe Arg Lys
        435                 440                 445

Ser Pro Gln Glu Leu Leu Cys Gly Ala Ser Leu Ile Ser Asp Arg Trp
        450                 455                 460

Val Leu Thr Ala Ala His Cys Leu Leu Tyr Pro Pro Trp Asp Lys Asn
465                 470                 475                 480
```

```
Phe Thr Glu Asn Asp Leu Leu Val Arg Ile Gly Lys His Ser Arg Thr
                485                 490                 495

Arg Tyr Glu Arg Asn Ile Glu Lys Ile Ser Met Leu Glu Lys Ile Tyr
            500                 505                 510

Ile His Pro Arg Tyr Asn Trp Arg Glu Asn Leu Asp Arg Asp Ile Ala
            515                 520                 525

Leu Met Lys Leu Lys Lys Pro Val Ala Phe Ser Asp Tyr Ile His Pro
        530                 535                 540

Val Cys Leu Pro Asp Arg Glu Thr Ala Ala Ser Leu Leu Gln Ala Gly
545                 550                 555                 560

Tyr Lys Gly Arg Val Thr Gly Trp Gly Asn Leu Lys Glu Thr Trp Thr
                565                 570                 575

Ala Asn Val Gly Lys Gly Gln Pro Ser Val Leu Gln Val Val Asn Leu
            580                 585                 590

Pro Ile Val Glu Arg Pro Val Cys Lys Asp Ser Thr Arg Ile Arg Ile
            595                 600                 605

Thr Asp Asn Met Phe Cys Ala Gly Tyr Lys Pro Asp Glu Gly Lys Arg
        610                 615                 620

Gly Asp Ala Cys Glu Gly Asp Ser Gly Gly Pro Phe Val Met Lys Ser
625                 630                 635                 640

Pro Phe Asn Asn Arg Trp Tyr Gln Met Gly Ile Val Ser Trp Gly Glu
                645                 650                 655

Gly Cys Asp Arg Asp Gly Lys Tyr Gly Phe Tyr Thr His Val Phe Arg
            660                 665                 670

Leu Lys Lys Trp Ile Gln Lys Val Ile Asp Gln Phe Gly Glu
        675                 680                 685

<210> SEQ ID NO 9
<211> LENGTH: 1084
<212> TYPE: PRT
<213> ORGANISM: Artificial Sequence
<220> FEATURE:
<223> OTHER INFORMATION: NusA-fused prothrombin

<400> SEQUENCE: 9

Met Asn Lys Glu Ile Leu Ala Val Val Glu Ala Val Ser Asn Glu Lys
1               5                   10                  15

Ala Leu Pro Arg Glu Lys Ile Phe Glu Ala Leu Glu Ser Ala Leu Ala
            20                  25                  30

Thr Ala Thr Lys Lys Lys Tyr Glu Gln Glu Ile Asp Val Arg Val Gln
        35                  40                  45

Ile Asp Arg Lys Ser Gly Asp Phe Asp Thr Phe Arg Arg Trp Leu Val
    50                  55                  60

Val Asp Glu Val Thr Gln Pro Thr Lys Glu Ile Thr Leu Glu Ala Ala
65                  70                  75                  80

Arg Tyr Glu Asp Glu Ser Leu Asn Leu Gly Asp Tyr Val Glu Asp Gln
                85                  90                  95

Ile Glu Ser Val Thr Phe Asp Arg Ile Thr Thr Gln Thr Ala Lys Gln
            100                 105                 110

Val Ile Val Gln Lys Val Arg Glu Ala Glu Arg Ala Met Val Val Asp
        115                 120                 125

Gln Phe Arg Glu His Glu Gly Glu Ile Ile Thr Gly Val Val Lys Lys
    130                 135                 140

Val Asn Arg Asp Asn Ile Ser Leu Asp Leu Gly Asn Asn Ala Glu Ala
145                 150                 155                 160
```

-continued

Val Ile Leu Arg Glu Asp Met Leu Pro Arg Glu Asn Phe Arg Pro Gly
                165                 170                 175

Asp Arg Val Arg Gly Val Leu Tyr Ser Val Arg Pro Glu Ala Arg Gly
            180                 185                 190

Ala Gln Leu Phe Val Thr Arg Ser Lys Pro Glu Met Leu Ile Glu Leu
        195                 200                 205

Phe Arg Ile Glu Val Pro Glu Ile Gly Glu Glu Val Ile Glu Ile Lys
    210                 215                 220

Ala Ala Ala Arg Asp Pro Gly Ser Arg Ala Lys Ile Ala Val Lys Thr
225                 230                 235                 240

Asn Asp Lys Arg Ile Asp Pro Val Gly Ala Cys Val Gly Met Arg Gly
                245                 250                 255

Ala Arg Val Gln Ala Val Ser Thr Glu Leu Gly Gly Glu Arg Ile Asp
            260                 265                 270

Ile Val Leu Trp Asp Asp Asn Pro Ala Gln Phe Val Ile Asn Ala Met
        275                 280                 285

Ala Pro Ala Asp Val Ala Ser Ile Val Val Asp Glu Asp Lys His Thr
    290                 295                 300

Met Asp Ile Ala Val Glu Ala Gly Asn Leu Ala Gln Ala Ile Gly Arg
305                 310                 315                 320

Asn Gly Gln Asn Val Arg Leu Ala Ser Gln Leu Ser Gly Trp Glu Leu
                325                 330                 335

Asn Val Met Thr Val Asp Asp Leu Gln Ala Lys His Gln Ala Glu Ala
            340                 345                 350

His Ala Ala Ile Asp Thr Phe Thr Lys Tyr Leu Asp Ile Asp Glu Asp
        355                 360                 365

Phe Ala Thr Val Leu Val Glu Glu Gly Phe Ser Thr Leu Glu Glu Leu
    370                 375                 380

Ala Tyr Val Pro Met Lys Glu Leu Leu Glu Ile Glu Gly Leu Asp Glu
385                 390                 395                 400

Pro Thr Val Glu Ala Leu Arg Glu Arg Ala Lys Asn Ala Leu Ala Thr
                405                 410                 415

Ile Ala Gln Ala Gln Glu Glu Ser Leu Gly Asp Asn Lys Pro Ala Asp
            420                 425                 430

Asp Leu Leu Asn Leu Glu Gly Val Asp Arg Asp Leu Ala Phe Lys Leu
        435                 440                 445

Ala Ala Arg Gly Val Cys Thr Leu Glu Asp Leu Ala Glu Gln Gly Ile
    450                 455                 460

Asp Asp Leu Ala Asp Ile Glu Gly Leu Thr Asp Glu Lys Ala Gly Ala
465                 470                 475                 480

Leu Ile Met Ala Ala Arg Asn Ile Cys Trp Phe Gly Asp Glu Ala Glu
                485                 490                 495

Asp Leu Tyr Phe Gln Ser Glu Phe Met Ala Asn Thr Phe Leu Glu Glu
            500                 505                 510

Val Arg Lys Gly Asn Leu Glu Arg Glu Cys Val Glu Glu Thr Cys Ser
        515                 520                 525

Tyr Glu Glu Ala Phe Glu Ala Leu Glu Ser Ser Thr Ala Thr Asp Val
    530                 535                 540

Phe Trp Ala Lys Tyr Thr Ala Cys Glu Thr Ala Arg Thr Pro Arg Asp
545                 550                 555                 560

Lys Leu Ala Ala Cys Leu Glu Gly Asn Cys Ala Glu Gly Leu Gly Thr
                565                 570                 575

Asn Tyr Arg Gly His Val Asn Ile Thr Arg Ser Gly Ile Glu Cys Gln

```
                580             585             590
Leu Trp Arg Ser Arg Tyr Pro His Lys Pro Glu Ile Asn Ser Thr Thr
            595             600             605

His Pro Gly Ala Asp Leu Gln Glu Asn Phe Cys Arg Asn Pro Asp Ser
610             615             620

Ser Thr Thr Gly Pro Trp Cys Tyr Thr Thr Asp Pro Thr Val Arg Arg
625             630             635             640

Gln Glu Cys Ser Ile Pro Val Cys Gly Gln Asp Gln Val Thr Val Ala
            645             650             655

Met Thr Pro Arg Ser Glu Gly Ser Ser Val Asn Leu Ser Pro Pro Leu
            660             665             670

Glu Gln Cys Val Pro Asp Arg Gly Gln Gln Tyr Gln Gly Arg Leu Ala
            675             680             685

Val Thr Thr His Gly Leu Pro Cys Leu Ala Trp Ala Ser Ala Gln Ala
            690             695             700

Lys Ala Leu Ser Lys His Gln Asp Phe Asn Ser Ala Val Gln Leu Val
705             710             715             720

Glu Asn Phe Cys Arg Asn Pro Asp Gly Asp Glu Glu Gly Val Trp Cys
                725             730             735

Tyr Val Ala Gly Lys Pro Gly Asp Phe Gly Tyr Cys Asp Leu Asn Tyr
                740             745             750

Cys Glu Glu Ala Val Glu Glu Thr Gly Asp Gly Leu Asp Glu Asp
            755             760             765

Ser Asp Arg Ala Ile Glu Gly Arg Thr Ala Thr Ser Glu Tyr Gln Thr
            770             775             780

Phe Phe Asn Pro Arg Thr Phe Gly Ser Gly Glu Ala Asp Cys Gly Leu
785             790             795             800

Arg Pro Leu Phe Glu Lys Lys Ser Leu Glu Asp Lys Thr Glu Arg Glu
                805             810             815

Leu Leu Glu Ser Tyr Ile Asp Gly Arg Ile Val Glu Gly Ser Asp Ala
                820             825             830

Glu Ile Gly Met Ser Pro Trp Gln Val Met Leu Phe Arg Lys Ser Pro
            835             840             845

Gln Glu Leu Leu Cys Gly Ala Ser Leu Ile Ser Asp Arg Trp Val Leu
            850             855             860

Thr Ala Ala His Cys Leu Leu Tyr Pro Pro Trp Asp Lys Asn Phe Thr
865             870             875             880

Glu Asn Asp Leu Leu Val Arg Ile Gly Lys His Ser Arg Thr Arg Tyr
                885             890             895

Glu Arg Asn Ile Glu Lys Ile Ser Met Leu Glu Lys Ile Tyr Ile His
                900             905             910

Pro Arg Tyr Asn Trp Arg Glu Asn Leu Asp Arg Asp Ile Ala Leu Met
            915             920             925

Lys Leu Lys Lys Pro Val Ala Phe Ser Asp Tyr Ile His Pro Val Cys
930             935             940

Leu Pro Asp Arg Glu Thr Ala Ala Ser Leu Leu Gln Ala Gly Tyr Lys
945             950             955             960

Gly Arg Val Thr Gly Trp Gly Asn Leu Lys Glu Thr Trp Thr Ala Asn
                965             970             975

Val Gly Lys Gly Gln Pro Ser Val Leu Gln Val Val Asn Leu Pro Ile
            980             985             990

Val Glu Arg Pro Val Cys Lys Asp Ser Thr Arg Ile Arg Ile Thr Asp
            995             1000            1005
```

Asn Met Phe Cys Ala Gly Tyr Lys Pro Asp Glu Gly Lys Arg Gly
1010                1015                1020

Asp Ala Cys Glu Gly Asp Ser Gly Gly Pro Phe Val Met Lys Ser
    1025                1030                1035

Pro Phe Asn Asn Arg Trp Tyr Gln Met Gly Ile Val Ser Trp Gly
1040                1045                1050

Glu Gly Cys Asp Arg Asp Gly Lys Tyr Gly Phe Tyr Thr His Val
1055                1060                1065

Phe Arg Leu Lys Lys Trp Ile Gln Lys Val Ile Asp Gln Phe Gly
    1070                1075                1080

Glu

<210> SEQ ID NO 10
<211> LENGTH: 32
<212> TYPE: DNA
<213> ORGANISM: Artificial Sequence
<220> FEATURE:
<223> OTHER INFORMATION: Synthetic Primer

<400> SEQUENCE: 10
aagaattcat ggccaacacc ttcttggagg ag                          32

<210> SEQ ID NO 11
<211> LENGTH: 35
<212> TYPE: DNA
<213> ORGANISM: Artificial Sequence
<220> FEATURE:
<223> OTHER INFORMATION: Synthetic Primer

<400> SEQUENCE: 11
aatctagact actctccaaa ctgatcaatg acctt                       35

<210> SEQ ID NO 12
<211> LENGTH: 30
<212> TYPE: DNA
<213> ORGANISM: Artificial Sequence
<220> FEATURE:
<223> OTHER INFORMATION: Synthetic Primer

<400> SEQUENCE: 12
aaggtaccat gaaaataaaa acaggtgcgc                             30

<210> SEQ ID NO 13
<211> LENGTH: 38
<212> TYPE: DNA
<213> ORGANISM: Artificial Sequence
<220> FEATURE:
<223> OTHER INFORMATION: Synthetic Primer

<400> SEQUENCE: 13
ttgaattcgc tctgaaagta cagatcctca gtctgcgc                    38

<210> SEQ ID NO 14
<211> LENGTH: 27
<212> TYPE: DNA
<213> ORGANISM: Artificial Sequence
<220> FEATURE:
<223> OTHER INFORMATION: Synthetic Primer

<400> SEQUENCE: 14
aaggtaccat gtccctgcag gactcag                                27

```
<210> SEQ ID NO 15
<211> LENGTH: 40
<212> TYPE: DNA
<213> ORGANISM: Artificial Sequence
<220> FEATURE:
<223> OTHER INFORMATION: Synthetic Primer

<400> SEQUENCE: 15
ttgaattcgc tctgaaagta cagatcctca atctgttctc                            40

<210> SEQ ID NO 16
<211> LENGTH: 40
<212> TYPE: DNA
<213> ORGANISM: Artificial Sequence
<220> FEATURE:
<223> OTHER INFORMATION: Synthetic Primer

<400> SEQUENCE: 16
aagaattcgc tctgaaagta cagatcctcc gcttcgtcac                            40

<210> SEQ ID NO 17
<211> LENGTH: 33
<212> TYPE: DNA
<213> ORGANISM: Artificial Sequence
<220> FEATURE:
<223> OTHER INFORMATION: Synthetic Primer

<400> SEQUENCE: 17
aaggtaccat gaacaaagaa attttggctg tag                                   33
```